United States Patent [19]

Fay et al.

[11] Patent Number: 5,149,972
[45] Date of Patent: Sep. 22, 1992

[54] TWO EXCITATION WAVELENGTH VIDEO IMAGING MICROSCOPE

[75] Inventors: Frederic Fay, Worcester, Mass.; Fernando Dellaville, Philadelphia, Pa.

[73] Assignee: University of Massachusetts Medical Center, Worcester, Mass.

[21] Appl. No.: 466,889

[22] Filed: Jan. 18, 1990

[51] Int. Cl.⁵ .......................................... G01N 21/64
[52] U.S. Cl. .............................. 250/461.1; 250/372
[58] Field of Search ................ 250/372, 461.1, 461.2, 250/365

[56] References Cited

U.S. PATENT DOCUMENTS

| | | | |
|---|---|---|---|
| 3,297,873 | 1/1967 | Hovnanian et al. | 250/372 |
| 3,507,987 | 4/1970 | Bosch | 250/372 |
| 4,284,897 | 8/1981 | Sawamura et al. | 250/461.2 |
| 4,744,667 | 5/1988 | Fay et al. | 250/461.1 |
| 4,752,140 | 6/1988 | Cielo et al. | 356/358 |
| 4,773,097 | 9/1988 | Suzaki et al. | 250/461.2 |
| 4,786,170 | 11/1988 | Groebler | 250/458.1 |
| 4,788,137 | 11/1988 | Reinherz et al. | 435/7 |
| 4,791,310 | 12/1988 | Honig et al. | 250/461.2 |
| 4,844,617 | 7/1989 | Kelderman et al. | 250/372 |

OTHER PUBLICATIONS

Fernando J. Delaville; Imaging Multi-Spectral Probes in Living Cells at Video Rates; Worcester Polytechnic Institute; Sep. 1989; (Thesis).

Joseph Y. Cheung et al.; Cytosolic Free Calcium Concentration in Individual Cardiac Myocytes in Primary Culture; American Journal of Physiology; 256:1120–1130; Jun. 1989.

John A. Connor et al.; Spatially Resolved Cytosolic Calcium Response to Angiotensin II and Potassium in Rat Glomerulosa Cells Measured by Dig. Imag. Tech.: J. Bio. Chem; 262:2919–27; Feb. 25, 1987.

Miller et al.; Erythropoietin Stimulates a Rise in Intracellular-Free Calcium Concentration in Single BFU-E Derived Erythroblasts at Spec. Stages of Diff.; Blood; Apr. 1989: 73: 1188–94.

Barbara A. Miller et al.; Erythropoietin Stimulates a Rise in Intracellular Free Calcium Concentration in Single Early Human Erythroid Precursors; J. Clin Invest; Jul. 1988; 82:309–15.

Stephen J. Quinn et al.; Calcium Response of Single Adrenal Glomerulosa Cells to External Potassium; American Physiological Society; pp. 488–495; 1988.

Takao Sugiyama et al.; Research Communications; vol. 141. No. 1; Nov. 26, 1986; pp. 340–345.

Michael J. Sepaniak et al.; Laser Two-Photon Excited Fluorescence Detection for High Pressure Liquid Chromatography; Analytical Chemistry; 49:1554–56; Sep. 1977.

William H. Schuette et al.; The Design and Operation of a Dual-Beam Long-Focal-Length Fluorometer for Monitoring the Oxidative Metabolism in vivo; Med. and Bio. Eng'g; Mar. 1976; pp. 235–238.

Roy Howard et al.; Correction for Gain Variation in Microchannel Plate Intensified Multichannel Detectors; Applied Spectroscopy; 40:1245–46; 1986.

P. J. Chandley; A Simple Technique for Reducing the Phase Jitter of a Light Chopper; Infrared Physics; vol. 22; pp. 311–312; 1982.

Primary Examiner—Carolyn E. Fields
Assistant Examiner—Drew A. Dunn
Attorney, Agent, or Firm—Fish & Richardson

[57] ABSTRACT

An imaging apparatus which includes: a fluorescent imaging microscope; a uv radiation source capable of producing a plurality of uv excitation wavelengths; a filter device to select a first and a second excitation wavelength from the plurality of uv excitation wavelengths; a sample chamber to hold a sample for illumination by the radiation of the first and second wavelengths; a photometer to measure the intensity of the excitation wavelength being selected by the filter device and to generate an intensity signal representative of the measured intensity; and a processor in communication with the photometer to record the intensity signal produced by the photometer.

9 Claims, 12 Drawing Sheets

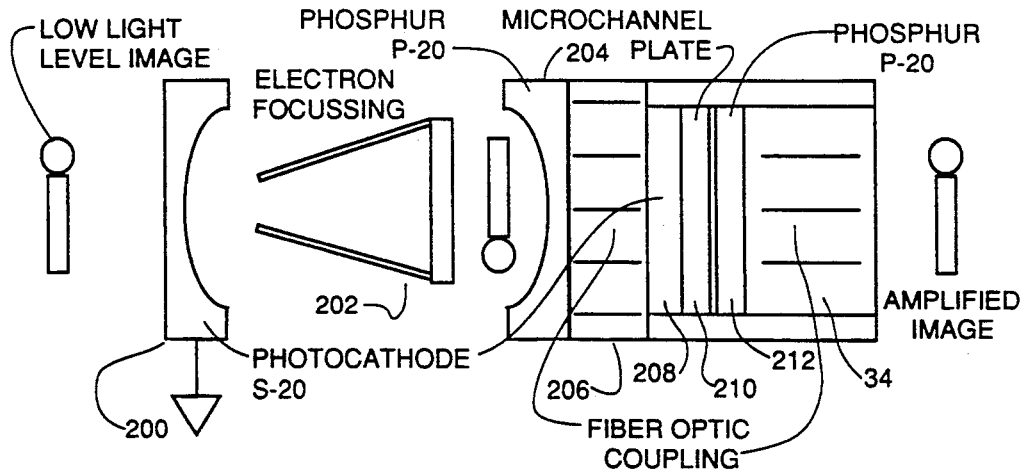
FIG 6
FIG 7
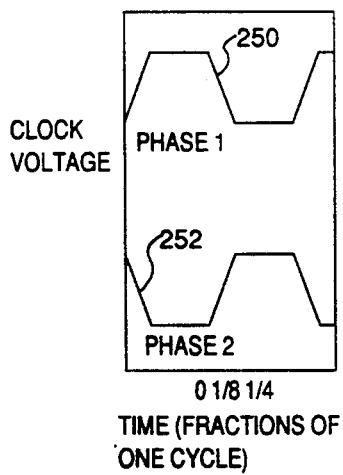
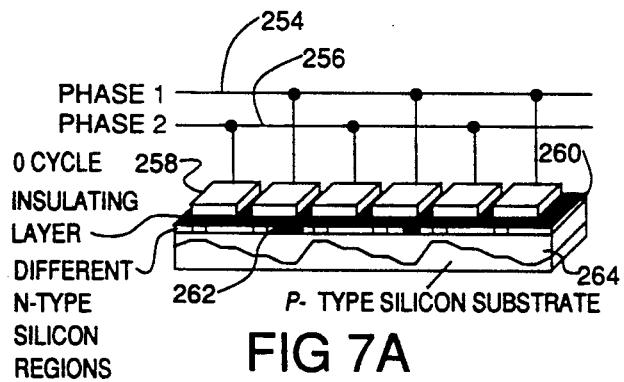
FIG 7A
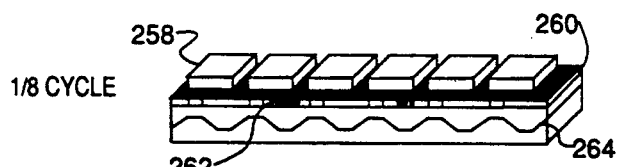
FIG 7B
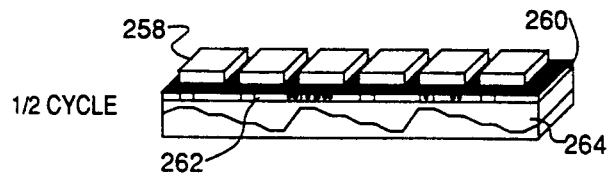
FIG 7C

INITIALIZATION ALGORITHM

1) COMMUNICATION IS ESTABLISHED BETWEEN THE COMPUTER AND THE ODR. ⟵ 400

2) A CORRECTION LOOK UP TABLE IS LOADED IN THE DIGITIZING BOARD TO LINEARIZE CAMERA INPUT. ⟵ 402

3) AN EMPTY SPACE APPROPRIATE FOR THE SIZE OF THE EXPERIMENT IS LOCATED IN THE ODR. ⟵ 404

4) THE USER IS GUIDED TO A MENU WHERE HE MAY SET ALL THE PARAMETERS OF THE EXPERIMENT, SUCH AS A NUMBER OF FRAMES, GAIN OF PHOTO-METER RECORDER, CALIBRATION INFORMATION, AND NAME OF FILE TO STORE EXPERIMENT INFORMATION. ⟵ 406

5) THE USER IS ALLOWED TO CHECK THE FLUORESCENT IMAGES BEFORE RECORDING IMAGES IN TWO DIFFERENT MODES, AS SINGLE FRAMES AS THE STROBE GIVES A TEN FLASH BURST, OR AS AVERAGED IMAGES OBTAINED BY ADDING SEVERAL ODD FIELDS TOGETHER FOR UP TO 128 TIMES. ⟵ 408

FIG 11

STORAGE ALGORITHM

DO n FROM 1 TO ITIMES

1) WAIT FOR THE BEGINNING OF EVEN FIELD, THEN WAIT FOR 20 HORIZONTAL BLANKING PERIODS (HBs) TO ALLOW FOR TRANSFER OF PREVIOUS FIELD FROM ACTIVE ZONE IN CCD CHIP. ⌐450

2) READ FILTER POSITION ⌐452

3) FIRE STROBE FLASH, THEN WAIT 2 HBs FOR PHOTOMETER INTEGRATION TO TAKE PLACE. ⌐454

4) READ VALUE FROM STROBE PHOTOMETER. ⌐456

5) WAIT FOR BEGINNING OF ODD FIELD, AND 20 HBs MORE ⌐458

6) FIRE STROBE FLASH, AND WAIT 2 HBs ⌐460

7) READ PHOTOMETER VALUE, AND SAVE IN ARRAY ⌐462

8) READ FILTER POSITION, IF SAME AS LAST NO FILTER POSITION ERROR OCCURRED. ⌐464

9) PUT MARKER ON IMAGE TO IDENTIFY WAVELENGTH OF EXCITATION (FILTER). ⌐466

10) IF n GREATER THEN 2 BUT LESS THAN (ITIMES-1) RECORD IMAGE IN ODR. THE FIRST TWO IMAGES WITHOUT FLASH CAN BE USED TO CALCULATE DARK CURRENT NOISE, AND THE LAST ONE HAS EXPERIMENT DATA FOR LATER REFERENCE. ⌐468

FIG 12

COMPLETION ALGORITHM

1) STORE DATA FROM PHOTOMETER ON FILE — 480

2) CREATE IMAGE WITH USER'S DATA AND PHOTOMETER STATISTICS TO BE SAVED AS LAST IMAGE OF EXPERIMENT — 482

3) RETURN CONTROL TO USER AND DISPLAY MENU — 484

FIG 13

TWO EXCITATION WAVELENGTH VIDEO IMAGING MICROSCOPE

BACKGROUND OF THE INVENTION

This invention relates to video imaging systems.

Basic research in cell biology and physiology is interested in isolating the different chemical participant molecules and understanding the working relationship between them.

For example, the role of calcium as a second messenger in a variety of cell responses is a prime target for this kind of study. A large calcium concentration gradient is preserved by pumps transporting the free $Ca^{++}$ ions out of the cell, or into calcium stores inside the cell. Due to the large concentration gradient, intracellular calcium levels can rise from 100 nM to above 1 $\mu$M in a matter of a few seconds. Therefore, quantitative spatial information that is minimally corrupted by motion artifacts or noise is necessary to study changes in Calcium concentration.

Fluorescent dye agents can be used to quantify the presence of distinct molecules within a population of whole cells or in isolated cell compartments. There is a wide availability of fluorescent tracers for specific proteins, lipids, and ions; as well as stains for different cell structures, and probes that change spectral properties with pH, or membrane potential.

Since cell responses to external stimuli may vary from the millisecond range to several hours, a sensitive digital imaging microscope together with the appropriate fluorescent labels permit an investigator to follow the target molecules spatially within the cell.

In principle, any two dyes that do not overlap in their excitation and emission spectra can be imaged in rapid succession. Ratiometric indicators, that require fluorescent distribution data at two different wavelengths, can provide reliable quantitative data.

Only a fraction of the absorbed photons will actually promote the emission of fluorescence photon. This fraction reflects any alternate ways of de-energizing and is dependent upon the fluorescent species and the excitation wavelength. This fraction is called the Quantum Efficiency (QE) and is always less than 1. This fraction is given by the relationship: Quantum Efficiency=Photons emitted/Photons absorbed So, the rate of fluorescent photon emission (F) is given by the equations:

$$F = QE \cdot K_a$$

where $K_a = I_o - I$ and is the rate at which photons are absorbed.

This can be rewritten as:

$$F = QE \cdot I_o \cdot (1 - exp(-(e \cdot c \cdot L)))$$

where (C) is the concentration of the molecules, (L) is the path length, (e) is the extinction coefficient and $I_o$ is the incident light intensity.

Using the series expansion equivalent for the exponential function this equation can be expanded:

$$Exp(X) = 1 + X + X^2/2! + X^3/3! + \ldots$$

For low concentrations (c) and short path lengths (L), the fluorescent intensity equation can be approximated by:

$$F \approx QE \cdot I_o \cdot e \cdot c \cdot L$$

It can be seen that the fluorescent intensity in photons per seconds is directly proportional to incident intensity, extinction coefficient, quantum efficiency, concentration, and pathlength.

With the advances in biochemistry over the last decade several fluorescent probes have been developed to study cells. Probes can be used to covalently label macromolecules or organelles in living and fixed cells. DNA, RNA, proteins and lipids can be labelled. Immunochemistry assays can produce fluorescently labelled antibodies that bind with a high affinity to specific protein receptors or enzymes. There is also another group of fluorescent probes that will change their fluorescent intensity o spectra following changes in specific ion concentrations, pH, membrane potential, etc.

It is thus now possible to study cell function by correlating the distributions of different molecules or ions simultaneously in single living cells. By labelling specific organelles, it is also possible to determine the redistribution of target molecules or ions after an experimental stimulus is applied. Local concentrations of target molecules or ions can be calculated by using probes that alter their fluorescent response in the presence of these chemical species.

The precise determination of local concentrations from fluorescent data in single cells is difficult due to the low fluorescence intensity that can be obtained from single cells. Even with the calibration curves that associate the intensity value detected to local concentration values, there are several sources of error. Changes in optical pathlength (thickness) in different regions of the cell, and any preferential distribution of the probe in different cell compartments will undermine the calculations.

Ratiometric indicators, that shift their spectral peaks upon binding ions such as calcium or sodium are now commercially available. With the use of these indicators, the local concentration of the ion can be calculated from data acquired at two different wavelengths.

Consider an ideal fluorescent probe that has only two possible configurations:

1) Bound to the ion target: With spectral peak at wavelength $L_1$
2) Unbound (free): With spectral peak at $L_2$ To make use of the largest shift in spectra, two wavelength measurements ($F_1$ and $F_2$) are made, corresponding to the spectral peaks, $L_1$ and $L_2$. It is important to note that the spectral curve of these dyes is usually very wide, and there is some overlap between the free and the bound species curves.

Since only two possible fluorescent states exist, any measurement of fluorescent intensity ($F_1$ and $F_2$) of a mixed solution (or loaded cell) will be the additive contributions from the fluorescence of the two species.

The fluorescence at wavelength 1 that is due to the free (f) and the bound (b) form of probe is given by the expression: $F_1 = F^f_1 + F^b_1$ Similarly, the fluorescence at wavelength 2 is given by the expression $F_2 = F^f_2 + F^b_2$ The unknown partial contributions: $F^f_1$, $F^f_2$, $F^b_1$, and $F^b_2$ are a function of excitation intensity ($I_o$), pathlength (L), concentration (c), quantum efficiency (QE), and extinction coefficient (e).

Letting $a = QE \cdot e$,

And $c^f$, $c^b$ = concentration of free and bound form of the probe respectively, then $$F_1 = \{(a_1^f * c^f) + (a_1^b * c^b)\} * I_0 * L$$

$$F_2 = \{(a_2^f * c^f) + (a_2^b * c^b)\} * I_0 * L$$

The chemical dissociation equation for the dye is:

$$c^b \rightarrow c^f + [ION]$$

Hence, $$Kd = c^f * [ION] / c^b$$

If the constant of dissociation (Kd) of the probe-ion binding equation is known, then the actual ion concentration ( [ION] ) is found by substituting this last equation as into the two previous equations before taking their ratio.

$$\frac{F_1}{F_2} = \frac{\{(a_1^f * c^f) + (a_1^b * c^f * [ION]/Kd)\} * I_0 * L}{\{(a_2^f * c^f) + (a_2^b * c^f * [ION]/Kd)\} * I_0 * L}$$

$$R = \frac{F_1}{F_2} = \frac{(a_1^f * Kd) + (a_1^b * [ION])}{(a_2^f * Kd) + (a_2^b * [ION])}$$

From the above equation it is seen that the ratio of fluorescence is independent of pathlength, intensity, and concentration of probe. The ratio is only a function of ion concentration ( [ION] ), which can be now calculated without regard to cell shape.

$$[ION] = \frac{\{R - a_1^f/a_2^f\} * Kd}{\{a_1^b/a_2^b - R\}} \cdot \frac{a_2^f}{a_2^b}$$

When calculating ion concentration from acquired data it is not necessary to consider any of these intermediate parameters constants, since it can be found from the ratio of fluorescence intensities. That is:

$a_1^f / a_2^f = F_1^f / F_2^f$ = ratio of fluorescence for the free form of the dye, $a_1^b / a_2^b = F_1^b / F_2^b$ = ratio of fluorescence for the bound form of the dye, and $a_2^f / a_2^b = F_2^f / F_2^b$ = ratio of fluorescence at wavelength 2.

Kd is the constant of dissociation and can be measured in solutions in vitro.

Another consideration is that the fluorescent dyes used to label living cells have to be introduced into the cell cytoplasm with a minimum of damage to cell function.

Some dyes can be made membrane soluble (non polar) by adding chemical species to their polar ends. The cells are then submerged in media containing the membrane soluble form of the dye for loading. After the dye diffuses from the media in which it is barely soluble into the cell membrane, enzymes inside the cell cleave the terminal species away leaving the fluorophor trapped inside the cell. This method provides the least disruptive approach to cell loading and has a greater cell survival rate.

For example, Fura-2 dye can be obtained in a free acid form and in the acetoxymethyl (AM) form. The free form is calcium-sensitive and not membrane-soluble, while the Fura-2 AM form can move into the membrane but does not respond to changes in calcium concentration. Intracellular esterases hydrolyze the AM form into the free acid form. The cells must not be overloaded with Fura-2 AM dye, as this will overwhelm the esterase capacity of the cell, and result in incomplete cleavage of dye which will affect the fluorescent measurements, since this intermediate form is highly fluorescent, but insensitive to local calcium concentration.

Fura-2 dye shifts the peak excitation from 380 nm to 340 nm when it binds to calcium. The equation for calcium concentration ([CA++]) requires the values for fluorescence intensity at the two wavelengths for both the calcium bound and the calcium free form of the dye. That is:

$$[Ca^{++}] = \{(R - Rmin)/(Rmax - R)\} * Kd * \beta.$$

where
$R = F_{340}/F_{380}$ = Ratio of fluorescence intensity in cell,
$Rmin = F^f_{340}/F^f_{380}$ = Ratio of fluorescence for free form of the dye,
$Rmax = F^b_{340}/F^b_{380}$ = Ratio of fluorescence for Calcium bound form of the dye,
$\beta = F^f_{380}/F^b_{380}$ = Ratio of fluorescence at 380 nm, and
Kd = Dissociation constant for Fura-2, which is approximately 220 nM in vitro.

To obtain the values for the constants: Rmin, Rmax, and $\beta$, fluorescent solutions with a known calcium and Fura-2 concentrations are imaged. The calcium free solution is made by adding the Ca++ chelator EGTA to the calibration solution, and Fura-2 free acid to a concentration of 1 to 4 micromolar. The calcium bound solution includes the sustaining media with extra calcium and the Fura-2 free acid. With these values, the grey levels obtained from the individual video images at each wavelength can be related to calcium concentrations inside the cell. Rmin, Rmax, and $\beta$ should be determined under the same chemical conditions (temperature, pH, concentration) and with the same optical components (objective, filters, and dichroic mirror) as the recorded images.

Commercial video cameras of the vidicon type require a photon flux greater than $10^8$ photons per millimeter squared per second to provide an "acceptable" (10.1 Signal to noise) image. Such cameras are generally too insensitive for detecting fluorescent images.

With the advent of the first generation image intensifiers in the 1960s, researchers use of intensified video cameras in microscopes for biological research. In the early 1970s, the Silicon Intensified Camera (SIT camera) pushed the sensitivity frontier to $10^7$ photons/mm2/sec. High quality intensified cameras and video recorders promoted a wider use among biological researchers. Second generation intensifiers, smaller and with simpler support electronics can be used as a first stage for a SIT camera (called an ISIT), with a sensitivity of $10^5$ photons/mm2/sec. SIT and ISIT cameras are used routinely to image fluorescent probes in living cells, but have problems of image persistence and geometrical distortion. Parallel advances in solid state technology in this decade have provided sensors like the charge coupled device (CCD), and charge injection device (CID) without the problems mentioned above. However, these sensors require an intensification stage to be used in low light level imaging at video rates (30 frames/second).

The development of the imaging technology was closely followed by biological applications. The fluorescent protein aequorin, which fluoresces when exposed to micromolar concentrations of calcium, was one of the first labels to be used in low light level microscopy. Experiments using aequorin showed that most of the calcium present in the cell in not in the free ion state, but sequestered, or stored inside. A sequence of images has been obtained which showed a "wave" of calcium spreading through the plasma membrane of a medaka fish egg upon fertilization. Other common fluorescent probes including "Rhodamine", "Texas Red", and "Fluorescein", have been attached to antibodies for proteins, lipids and other macromolecules. Many researchers have studied cell function, structure and vitality using the newly available instrumentation and fluorescent probes. Most of these studies required the averaging of several video frames to obtain an image with a good signal to noise ratio (SNR), and the processes being studied were not fast enough that this averaging would pose a problem.

SUMMARY OF THE INVENTION

One aspect of the invention is an apparatus for measuring the concentration of an ion in a sample. The apparatus includes a fluorescent imaging microscope, a uv radiation source capable of producing a plurality of uv excitation wavelengths, a filter device to select a first and a second excitation wavelength from the plurality of uv excitation wavelengths, the first excitation wavelength capable of exciting fluorescence by the ion in one valence state and the second excitation wavelength capable of exciting fluorescence by the ion in a second valence state, a sample chamber to hold a sample for illumination by the radiation of the first and second wavelengths, a photometer to measure the intensity of the excitation wavelength being selected by the filter device and to generate an intensity signal representative of the measured intensity, a beam splitter to direct a portion of the intensity of the selected wavelength onto the sample to be measured and to direct a second portion of the intensity of said selected wavelength the said photometer, optical elements to collect the fluorescent light emitted by the sample, an image intensifier positioned to receive the fluorescent light collected by the optical elements and to produce a intensified image of the sample, a video camera to view the intensified image and to produce an electronic signal representative of a frame of the image, a frame digitizer to digitize the frame of the electronic signal, a synchronizer in communication with the filter device and the video camera to synchronize the selection of one of the excitation wavelengths with the beginning of the production of the frame of said electronic signal by the video camera, and a processor in communication with the uv radiation source and the photometer to control the intensity of the uv radiation source and to record the intensity signal produced by the photometer, the computer also in communication with the frame digitizer to process the frame digitized by the frame digitizer and store the processed results on a disk.

A feature of one embodiment of the invention is that the uv radiation source has a fast rise-time. Another feature is that uv radiation source is a uv strobe or a uv laser and the filter means is a rotatable filter wheel. Another feature is that the beam splitter is a dichroic mirror. The synchronizer further includes a filter position sensor to determine which excitation wavelength is being selected and the synchronizer is in communication with the processor. The synchronizer comprises a differential amplifier having a first input terminal and a second input terminal, the first input terminal to receive a video synch pulse from the video camera and the second input terminal to receive a position signal from the filter position sensor. The differential amplifier produces an error signal in response thereto.

Another aspect of the invention is an imaging apparatus including a fluorescent imaging microscope, a uv radiation source capable of producing a plurality of uv excitation wavelengths, a filter device to select a first and a second excitation wavelength from the plurality of uv excitation wavelengths, a sample chamber to hold a sample for illumination by the radiation of the first and second wavelengths, a photometer to measure the intensity of the excitation wavelength being selected by the filter device and to generate an intensity signal representative of the measured intensity, and a processor in communication with the photometer to record the intensity signal produced by the photometer.

Features of the invention include the radiation source having a fast rise time. The processor is also in communication with the radiation source to control the switching of the source. A beam splitter is included to direct a portion of the radiation of the first wavelength onto a sample to be measured and to direct a second portion of the radiation of said the wavelength onto the photometer.

A further aspect of the invention is an imaging apparatus including a fluorescent imaging microscope, a sample illuminating uv radiation source capable of producing a plurality of uv excitation wavelengths, a filter device to select a first and a second excitation wavelength from the plurality of uv excitation wavelengths, a sample chamber to hold a sample for illumination by the radiation of the first and second wavelengths, optical elements to collect the fluorescent light emitted by the illuminated sample to form an image, a video camera to produce an electronic signal representative of a frame of the image, and a synchronizer in communication with the filter device and the video camera to synchronize the selection of the first excitation wavelength with the beginning of the production of the frame of said electronic signal by the video camera.

A feature of the invention is that the synchronizer further includes a position detector for generating a position signal in response to the beginning of the selection of the first wavelength. The synchronizer produces an error signal for correcting the selecting of the wavelength in response to the position signal and the electronic signal.

Still another aspect of the invention is an imaging apparatus including a fluorescent imaging microscope, a pulsed uv radiation source capable of producing a plurality of uv excitation wavelengths, a filter device to select a first and a second excitation wavelength from the plurality of uv excitation wavelengths, a sample chamber to hold a sample for illumination by tee radiation of the first and second wavelengths, a processor in communication with the radiation source to control the switching on and off of the radiation source in synchrony with the selection of the first and second excitation wavelengths by the filter device.

Another aspect of the invention is an imaging apparatus including a fluorescent imaging microscope, a pulsed uv radiation source capable of producing a plurality of uv excitation wavelengths, a filter device to select a first and a second excitation wavelength from the plurality of uv excitation wavelengths, a sample chamber to hold a sample for illumination by the radiation of the first and second wavelengths, and a video camera to produce an electronic signal representative of a frame of an image of the sample, the uv radiation source having a rise-time sufficiently fast as to produce a predetermined intensity prior to the production of the frame of said image.

DESCRIPTION OF THE PREFERRED EMBODIMENTS

This invention is pointed out with particularity in the appended claims. The above and further advantages of this invention may be better understood by referring to the following description taken in conjunction with the accompanying drawings, in which:

FIG. 6 is a block diagram of an embodiment of the image intensifier of FIG. 1;

FIG. 7 is a timing diagram of an embodiment of the CCD of FIG. 1;

FIGS. 7A–7C are schematic diagrams of embodiments of the CCD of FIG. 1;

FIG. 11 is a flow diagram for an embodiment of the system initialization algorithm for the system shown in FIG. 1;

FIG. 12 is a flow diagram for an embodiment of the storage algorithm for the system shown in FIG. 1;

FIG. 13 is a flow diagram for an embodiment of a completion algorithm for the system shown in FIG. 1;

Figure 1:
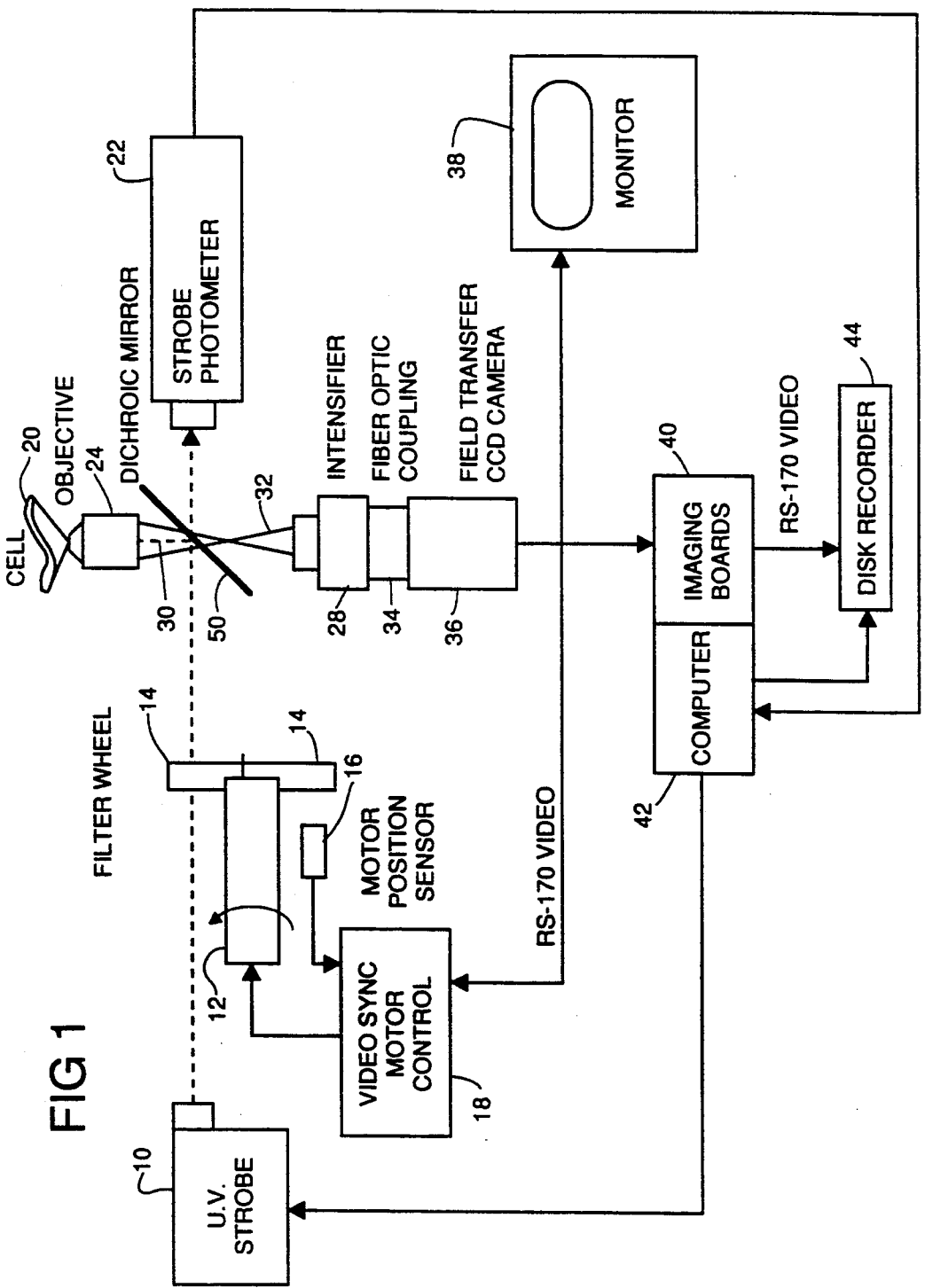
FIG. 1 is a block diagram of an embodiment of the invention.

A goal of the imaging apparatus of the invention is to be able to follow changes in molecule or ion concentrations in single living cells. The cell is loaded with a dual-spectral dye, such as Fura-2 ($Ca^{++}$) or SMBI ($Na^+$) and then excited by alternating wavelengths. The fluorescent emission from the cell is imaged using a low level camera assembly and the images stored for future processing.

To accomplish the minimum time resolution required to assess local changes in ion concentration in response to stimuli, about 100 milliseconds, the individual frames used in the ratiometric formula should be acquired as fast as possible.

The ratiometric dyes require two individual wavelength images to calculate the ion concentrations on a pixel by pixel basis. The two "raw" images should be obtained in a fast sequence to avoid excessive movement of the cell within them, since this will result in a motion artifact in the processed image. This motion artifact appears as bright or dark shadows, usually next to the boundary of the cell.

The invention solves this problem by alternating the excitation wavelength for every single frame. Individual raw images taken at the same wavelength may be added together at processing time to improve signal to noise ratio. The resulting averaged images will still provide a relatively motion-free ion image, because the data were alternatively accumulated for both wavelengths during the time window of study. Previous attempts to image fast moving cells using dual wavelength dyes were unsuccessful in this regard since they involved accumulating data at one wavelength, changing filters, and then imaging at the other. Significant motion artifacts could occur if the cell had moved or otherwise started to respond to fast intracellular chemical changes.

The dyes used in the cells to trace the target molecule are, in principle, innocuous, but if used in large quantities could affect the outcome of the experiments being performed. The amount of ultraviolet power being radiated on to the cell to excite the fluorophor is restricted, since an overdose could promote the generation of toxic byproducts, such as singlet oxygen and hydrogen peroxide. Accumulation of such substances will jeopardize the viability of the cell under study. Also, the fluorophor molecule will suffer decomposition (photobleaching) upon continuous irradiation with U.V. light. The presence of the photobleached species of the dye induces a measurement error because the chemical intermediates in this process are less fluorescent and are insensitive to changes in ion concentration.

The fluorescent output emission is directly proportional to the concentration of the dye and the excitation intensity. A very sensitive detector is needed to image the fluorescent distribution because of the low photon count arriving at the sensor level. According to our experimental measurements, the photon flux arriving at the detector has an intra-scene luminance range of about 900 to 9000 photons/$\mu m^2$ in a single strobe flash (one field of video). These measurements were made with calibration solutions of Fura-2 dye in the $Ca^{++}$ bound and free form. The solutions had a concentration of 4 $\mu M$ and are roughly equivalent in fluorescent intensity to successfully loaded cells. The cells are loaded with a dye concentration of approximately 150 $\mu M$, which provides enough signal for individual frame imaging, without significant buffering of the free $Ca^{++}$ within the cell.

The changes in ion concentration have to be followed in two dimensional space as well as over time, in order to answer questions about local propagation and/or displacement of ions. For example, second messengers ions, such as $Ca^{++}$ must be regulated locally inside the cell to promote concerted movement in muscle cells.

A minimum resolution of approximately one micron is required to be able to visualize any significant changes and relate them to structural features within the cell. In this manner, comparisons between concentrations in different organelles can be studied, as well as ion gradients within the cell cytoplasm.

It has been previously stated that the image acquisition process should be fast (at least video rates) after cell stimulation. To complete the experimental data it is also necessary to follow the same cell through the relaxation process, until it returns to the stable unexcited state.

Such a study generates a large amount of data, which can not be handled digitally without very expensive storage media. The system proposed is capable of storing at least 4 minutes of data, so that quantitative comparisons can be made of the same cell as it undergoes cycles of excitation-relaxation. It is also important to present the processed data in a manageable manner, such as a "movie" or sequence of two dimensional images through time. This kind of presentation allows the viewer to check for possible motion artifacts and to locate frames of particular importance in the experiment, that may require further processing or analysis.

A block diagram of the two wavelength excitation video microscope is shown in FIG. 1.

The design is centered around an epifluorescent microscope 24, to which special optical components and electronic hardware has been added. A computer 42 (Digital Equipment Corporation PDP 11/73) with analog inputs/outputs is used to control the image acquisition process and to serve as a host for the image acquisition and processing boards 40. For a light source we used a Xenon arc strobe 10 whose output is filtered by interference filters 14. These filters are mounted on a spinning wheel connected to the shaft of a d.c. motor 12 running at 15 revolutions per second. An analog feedback circuity 18 synchronizes the filter rotation speed with the video frequency of the camera 36, assuring the switching between selected wavelengths for every frame throughout the recording. The incoming U.V. light 20 is reflected 30 by the dichroic mirror 50 to the sample 26. The longer wavelength fluorescent emission 32 is transmitted through the mirror 50 and relayed by the optics to the intensified camera 37. The intensity of every flash of the strobe is monitored by a photodiode 22 located behind the mirror 50.

The intensifier-camera assembly 37 is sensitive enough to capture the faint fluorescent images from the cells. The video signal is stored on an optical disk recorder 44 for future processing.

The source of ultraviolet light 10 used to excite the cell samples is a pulsed Xenon arc lamp (model Strobex 236, Chadwick Helmuth). The spectral content and output power of an arc bulb discharge is dependent upon many factors such as electrode voltage, gas mixture, temperature and pressure. Inside the gas filled bulb, a steady flow of electrons is forced to jump through a gap between two electrodes. The collisions between electrons and the gas atoms promote the ionization of the gas with the subsequent transitions of gas electrons to higher energy levels. As these electrons descend to more stable ground state levels they give off energy in the form of radiated light. The additive combination of the different transitions will produce the overall shape of the output spectra. In the case of most gases output power is concentrated over a narrow range of wavelengths, corresponding to the most common transitions of electron energy levels. Advantages of Xenon bulbs are that, when ionized, there is almost complete separation between the Xenon atoms and their electrons, several energy level transitions are promoted simultaneously, and the output spectral curve is relatively flat from the ultraviolet range through the visible. Temperature affects the spectral output by increasing the infrared content as the bulb gets hot. Increasing the pressure of the gas, on the other hand, shifts the curve towards the ultraviolet. A gas pressure of approximately 10 atmospheres is typical for commercial grade bulbs.

Figure 2:
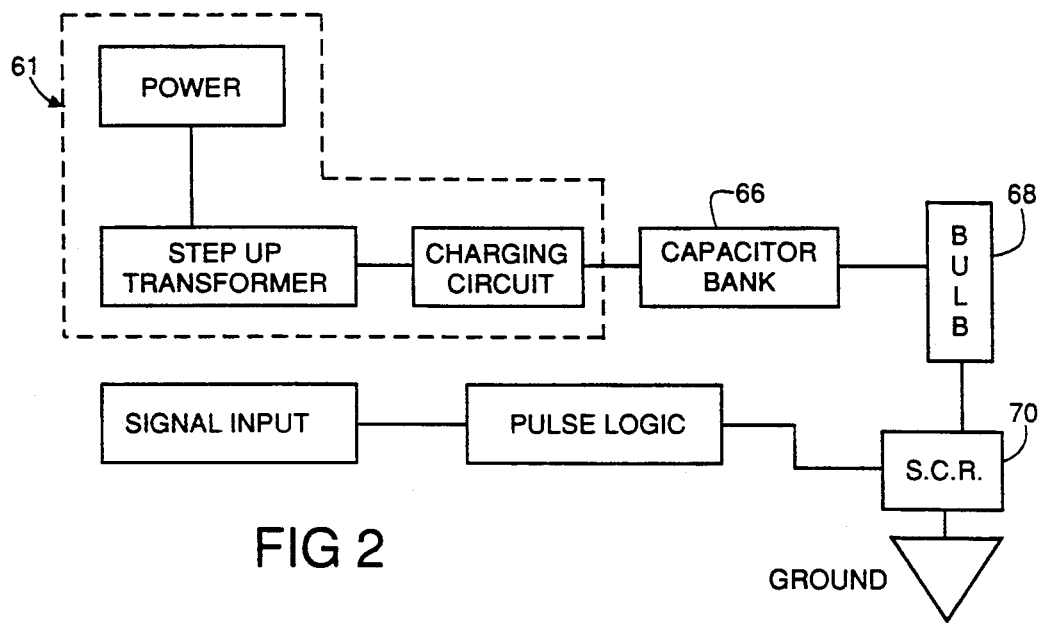
FIG. 2 is a block diagram of an embodiment of the UV source of FIG. 1.

Referring to FIG. 2, to use the Xenon bulb in a non-continuous manner, the power supply circuitry 61 charges a capacitor bank 66 to several hundred volts, and then allows it to discharge rapidly through the arc 68. For every flash cycle a silicon controlled rectifier (S.C.R.) 70 is activated with a pulse. This closes the path for the discharge of the capacitor 66 through the S.C.R., 70 passing through the electrode gap in the bulb 68, to the ground level. In the process of generating the light flash considerable amount of electromagnetic (EM) noise is produced. This EM noise was enough to contaminate the video signal from the camera, and to induce failure in the computer board generating the strobe firing pulse. To avoid these problems the strobe power supply 61 and arc bulb 68 housing are to be shielded in a metal box, with the chassis connected to earth ground. Also, the wiring between the computer output and the strobe was optically isolated with the use of a fiber optic cable.

Due to the constant of the capacitor charging circuit 61 there is an upper limit to the frequency of flashes for a given energy setting. The energy of the flash ranged from 30 Joules at 0.5 Hertz to 0.36 at 200.0 Hertz.

In one embodiment we are using the 1.44 joule per flash setting at a rate of 60 Hz (one flash per field). As a comparison, a continuous 75 Watt arc source typically delivers 1.25 joules in a filed period (16.6 milliseconds). Driving the system at a 60 Hz rate slightly overloads the manufacturer's suggested rate of 50 Hz. This will result in a shorter life period for the arc bulb.

The efficiency of delivery of the luminescent power is critically dependent on alignment of the flash beam to the objective of the microscope.

The output of the strobe has to be filtered in order to extract the narrow bands of excitation needed for the biological fluorescent probes. Most of the output power delivered by the source is not used to excite the sample. Xenon bulbs were still considered a better choice over pulsed lasers because they allow easy change of excitation wavelengths simply by changing the interference selection filters. Different fluorescent probes can be used by changing the filter disk appropriately. Pulsed lasers have very narrow specific spectral lines, so all their energy can be concentrated at the wavelengths of interest. Lasers that can be pulsed at 60 Hz rates, however, are typically more expensive than the Xenon arc strobe; and they do not permit easy switching to other working wavelengths. To generate the two wavelengths of interest requires either two lasers, or at least one laser and a laser dye module that would generate the other spectral line.

The two interference filters used for wavelength selection are mounted as complementary semicircles in a rotating wheel 14. The axis of rotation is connected to the shaft of a permanent magnet d.c. motor 12 through a 2:1 ratio gear box. The d.c. motor speed is proportional to the voltage across the armature. The motor housing includes an optical emitter-detector pair 16 to identify which filter is in the optical path of the microscope. As the motor and filter wheel are turning at a constant rate a tachometer square wave alternating from zero to +5 volts is generated (FILTACH). This (FILTACH) signal is used by the motor control circuitry 18, and read by the computer 42, so a reference marker is placed in every 380 nm image.

Figure 3:
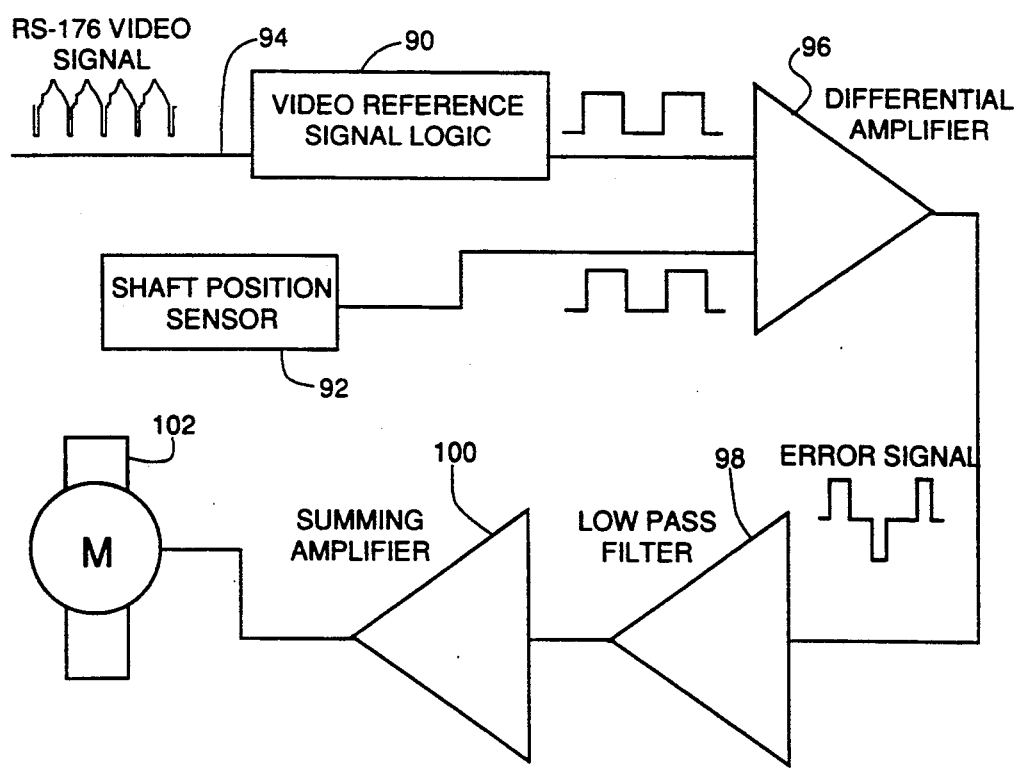
FIG. 3 is a block diagram of an embodiment of the video/synch motor control of FIG. 1.
Figure 16:
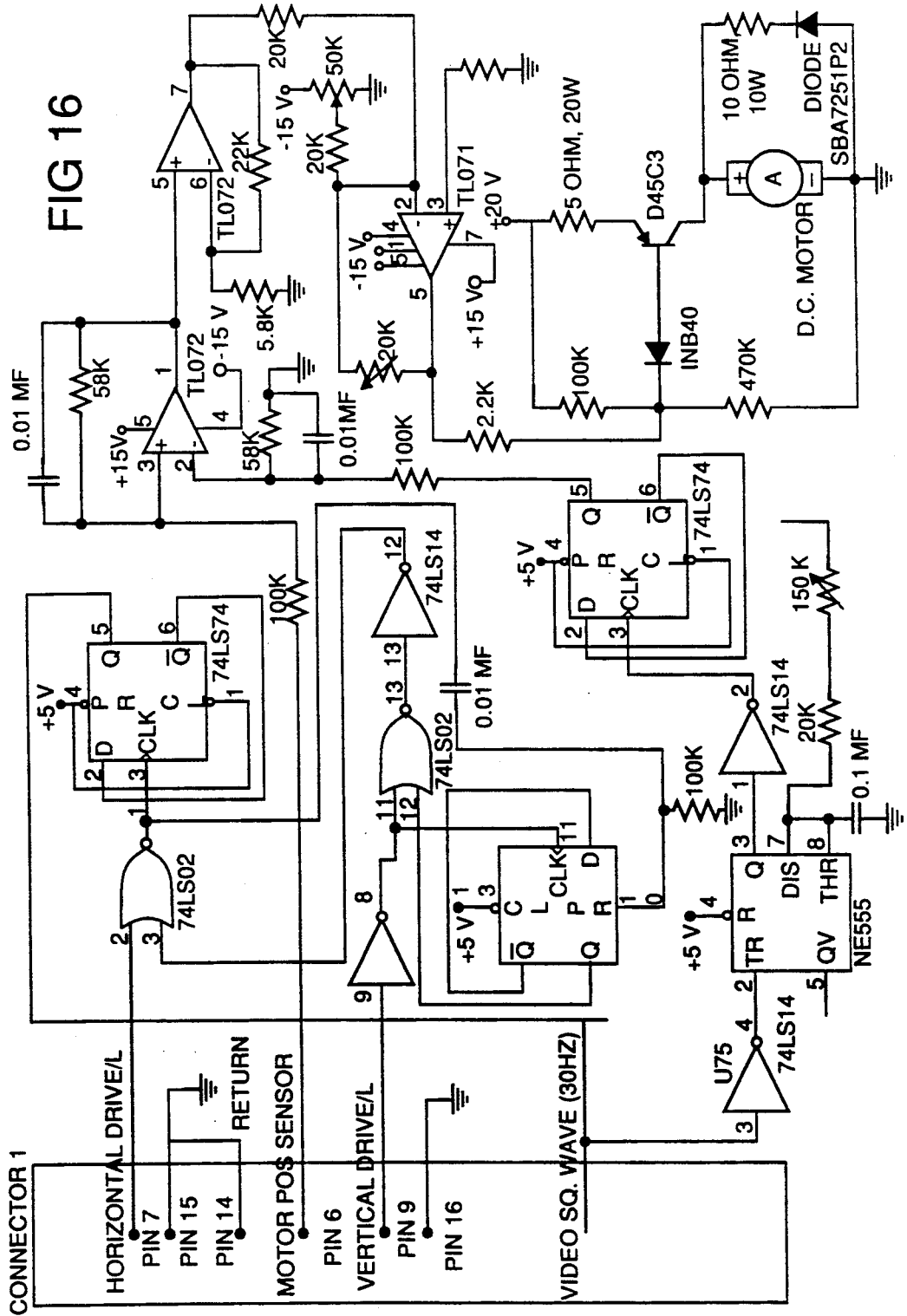
FIG. 16 is a schematic diagram for an embodiment of the video/sync controller for the embodiment of the system shown in FIG. 1.

In order to assure the proper switching between wavelengths of excitation on each frame requires a feedback control circuit. Referring to FIGS. 3 and 16, the controller was constructed on a wire-wrapped board with the low power circuitry, located in the computer case. The power stage that drives the motor is located in a box attached to the filter motor housing. First, a square wave with a frequency of 30 Hz is generated from the sync pulses 94 of the video signal. This video square wave, with transitions at the beginning of every even field is fed to a delay one-shot circuit 90. The phase of the output video square wave can then be set by varying a potentiometer on the circuit board. The phase displaced signal (VIDEO_REF) is then used as a reference signal for the proportional control circuitry. A low pass differential amplifier 96 generates an error signal by comparing the VIDEO_REF signal with the FILTACH signal 92. The error signal (ERR) is then proportional to the difference of the reference signal and the actual motor speed/position signal. This error signal is then passed through an offset amplifier 98 before the power stage 100, which actually drives the motor. The power driving stage uses a PNP bipolar transistor with proper biasing components and a protection diode against back EMF surges on motor turn on/off. The rotation of the motor completes the feedback loop through the optical position sensor 16. An optimal equilibrium control point is reached when the driving signal is running with equal positive and negative displacements for the baseline. Since the reference signal can be shifted in phase at will, any phase position is obtainable and stable for steady motor rotation. This approach to proportional control assures that both speed and phase relationships are maintained. The control requirements are quite stringent, since two flashes are made per filter position, see FIG. 4, a 33.5 degree wander would give us incorrect positioning of the filters at flash time.

The filters in the rotating wheel are characterized as a 340 nm and a 380 nm. The timing is set under computer control so that two flashes fall in each filter position, corresponding to each filed of the video signal, odd and even. This allows change of the wavelength of excitation on each frame of video.

Figure 5:
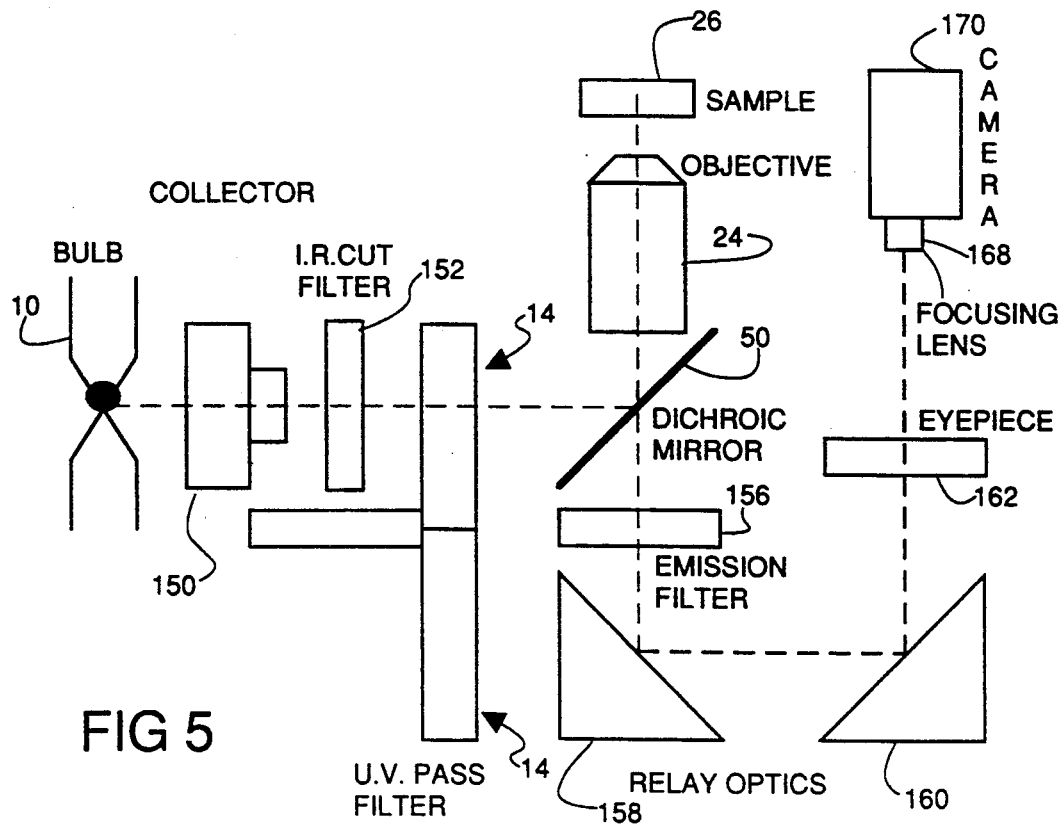
FIG. 5 is a block diagram of an embodiment of the optical element of FIG. 1.

Imaging fluorescent molecules that excited in the ultraviolet region of the spectra require special optics. FIG. 5 is an overview of the optical components needed for fluorescent microscopy.

Fluorescent probes, as explained in the previous chapter, emit light at a higher wavelength (lower energy) then the excitation radiation. A dichroic mirror 50 is used in the microscope to separate the excitation from the emission path according to wavelength. All optical elements in the illumination path must be UV transmissive.

The main elements in the epifluorescent microscope are: Illuminator 10, Excitation filters 154, Dichroic mirror 50, Objective 24, Emission filters 156, and Eyepiece 162.

The illuminator consists of the arc bulb, spherical mirror and collector, the mirror behind the bulb is positioned to have its focal point at the electrode arc position, therefore reflecting back most of the radiation falling away from the collector lens 150. The collector lens adjustments along the optical train axis permits focusing of the light source image further along the path. For Kohler illumination, the image of the arc should be placed at the level of the objective aperture plane. The Kohler method has the advantage of producing an homogeneous flat field of illumination at the sample level, because of the Fourier conjugate relationship between the aperture plane of the objective and the sample plane.

A set of filters is placed in the optical path after the illuminator. First an infrared reject filter 152 to cut down on any heat from the source hitting the ultraviolet interference filters 14 (which could be damaged by it). Also important is to minimize any I.R. radiation that could leak through to the photocathode of the image intensifier, since it is specially sensitive in this portion of the spectrum. Secondly, the U.V. bandpass filters 154 positioned in the rotating wheel alternate, selecting the excitation wavelength between 340 nm and 380 nm.

A dichroic mirror 50 placed under the objective 24 at a 45 degree angle, has a transmission curve which is wavelength dependent. The excitation U.V. light is reflected at 90 degrees through the objective 24 to the sample 26. However, the emission signal from the sample 26 can pass through the mirror 50 with high efficiency towards the camera port. The combined alignment of the bulb position, collector focus, and dichroic mirror angle is the key to a strong, uniform sample illumination.

The objective 24 in an epifluorescent microscope plays the double role of an illumination condenser, and magnifying lens. It is the most important component of the optical system and it should be free of chromatic aberrations and have a high numerical aperture. The figure of merit for the objective is the numerical aperture (NA), which is defined as:

$$NA = n' * \sin(theta)$$

Where n' is the refractive index of the medium and theta is the half angle of collection. Excellent objectives with numerical apertures of the order of 1.3 are available. They use immersion fluids such as oil or glycerine between the objective lens and the sample cover slip. The collection efficiency in these settings is proportional to the fourth power of the numerical aperture, which indicates its importance in light limited situations such as the imaging of living single cells.

Another interference filter 156 is used in the emission path after the dichroic mirror. Its transmission is centered at the peak emission wavelength of the probe and has a width narrow enough to minimize any leak from the excitation path, and avoid excessive signal from other sources such as cell autofluorescence. The actual width is a compromise between rejection of unwanted signal (autofluorescence), and efficient collection of the probe's emitted light. The autofluorescence signal peaks around 400 nm and diminishes rapidly with increasing wavelength. The width at half maximum for the emission filter is 140 nm.

The eyepiece 162 or ocular is the next magnification element and is placed just before the camera sensor or eyeport. When used in projection mode, the eyepiece 162 and focusing lenses 168 create a real image of the sample in the plane of the sensor of the camera 170. When used for human viewing, a magnified virtual image is seen by the user through it. The total magnification at the camera sensor level is the product of objective magnification times the ocular magnification.

An image intensifier (I.I.) is needed to provide enough gain to the signal from the cells so that the camera detector can record an image with acceptable signal to noise.

As shown in FIG. 6, one embodiment of an image intensifier has two stages: a first generation intensifier coupled by a fiber optic faceplate to a second generation intensifier. This combination provides very high gain (300,000 maximum).

The image intensifier has a S-20 photocathode 200 where incoming photons liberate photoelectrons at the inner surface, which are later accelerated by a high voltage potential difference to the anode. They are kept in focus by electromagnetic lenses 202, and as they strike the phosphor 204 at the output stage with increased potential energy, excite the phosphor crystals to liberate photons (phosphorescence). This produces an image fifty to one hundred times brighter after the first generation I.I.. The fiber optic faceplate 206 between intensifiers optimizes light transmission while keeping the image in focus with little resolution loss. The second stage I.I. amplifies the signal by electron multiplication, and is based on microchannel plate technology. The electrons liberated from the photocathode 208 kick out secondary electrons as they travel through the miniature electron multiplying channels of the wafer plate 210. Finally these electrons hit a second phosphor screen 212, to release visible photons. Gains of roughly 10,000 are easily obtained at this stage which are controllable with an external potentiometer.

The output phosphor crystals can be saturated by excessive input (resulting from a strong light source or a high II gain setting) giving rise to a long persistence of the image. This phosphorescence phenomena is sue to the excitation of outer electrons into higher energy orbitals in a triplet state (2 outer electrons with the same spin). The lowest transitional state of the triplet system will result in a response time of the order of milliseconds. If many electrons are overexcited into a higher transitional state, there will be a time "lag" before these electrons are lowered into the light emitting state.

This persistence can be considerable even after one video field, so special care is taken by the software to monitor the extent of the "lag" to avoid non-linear responses to light input. If it is not taken into account, the brightness of any section of an image at frame (n) can be affected by the previous frame (n−1). The noise generated at this level is mostly temperature dependent. Photocathode noise increases an order of magnitude for every 10 degree centigrade increase in temperature. Therefore the first photocathode area is cooled with a refrigerant bath to a temperature of −15 degrees centigrade. To avoid the condensation of water in the optical path dry air is continuously circulated in the space between the photocathode and the focusing lens of the camera.

Figure 8:
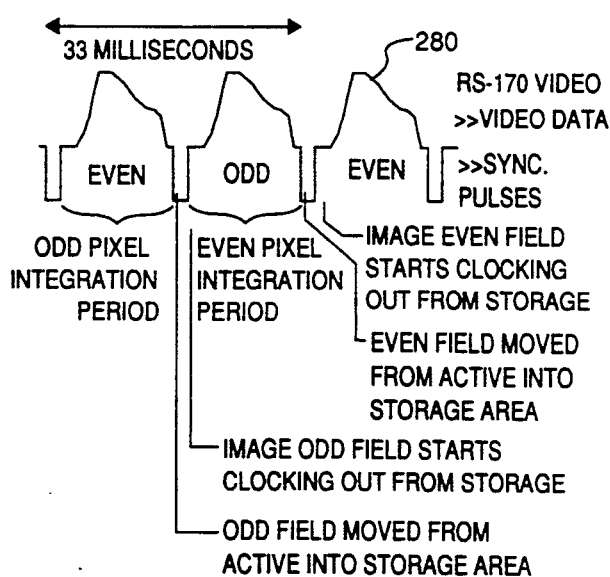
FIG. 8 is a timing diagram for the data transfer in a CCD for the embodiment of the invention shown in FIG. 1.
Figure 8A:
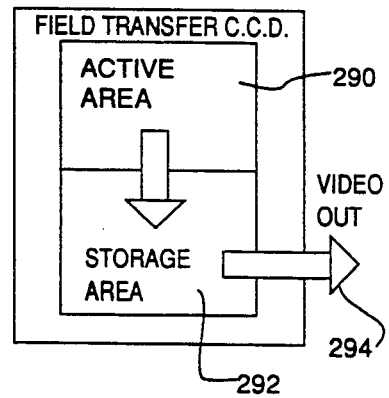
FIG. 8A is a block diagram of the data transfer in a CCD for the embodiment of the invention shown in FIG. 1.

A field transfer CCD video camera 36 is placed at the output of the image intensifier 28 (FIG. 1). It is coupled by a fiber optic faceplate 34 between the output phosphor 212 (FIG. 6) of the image intensifier and the sensor of the camera 36. The sensor of the camera chosen is a charge coupled device (CCD) integrated circuit. Referring to FIG. 7A, an imaging CCD chip consists of an array of identical "electron wells" capable of accumulating free electrons as packets in response to incoming light. A thick layer of p type material 264 (with hole carriers) in a "p-type" CCD is laid under a thinner n type (electron carriers) layer 260. Above the n type layer there are several gates 258 arranged geometrically throughout the surface, and with their inputs connected in a two phase 254, 256 clock arrangement. As the voltage in the gates 258 increases a deeper well (more favorable to attract free electrons) is created under it. If the sensor is in the focus plane of the optics, then the variations in illuminance at the sensor reflect luminance changes at the object plane. During the integration cycle of the wells, free electrons 262 will be stored in each well (corresponding to each pixel), proportionally to the illuminance cast upon it. These wells can move dynamically by the interaction of the different layers of semiconductors with the surface electrode gates voltages (FIGS. 8 and 8A). By clocking the gate signals, the electron packets are shifted out in a sequential manner with very high transfer efficiencies (99.995%).

The PULNIX 840N camera is used in one embodiment because of its field transfer architecture, and high sensitivity. This camera has an area sensor with 840 * 490 (horizontal * Vertical) pixels, arranged in two distinct zones. The pixels in the integrating zone will integrate the light input during a field cycle (16 milliseconds), then will be rapidly clocked out in the vertical direction into a storage zone during the vertical blanking (VB) period of 1 millisecond. After the blanking period, integration can start again, now with the pixels of the other field. FIG. 7 shows the timing of these events in the video signal and how odd and even fields interlace to form a total image.

Figure 9:
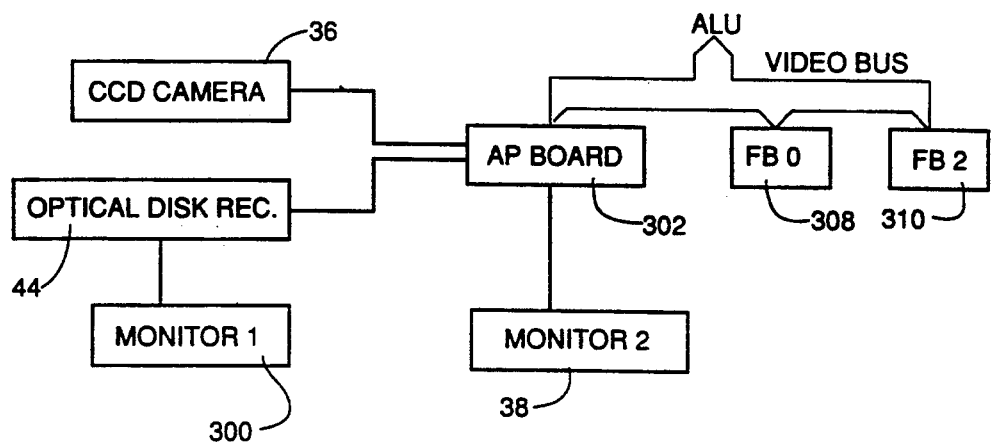
FIG. 9 is a block diagram of an embodiment of the imaging boards shown in FIG. 1.

The image detected by the C.C.D camera is stored for acquisition and processing purposes in a series of imaging boards FIG. 9. In one embodiment, the data is stored using one 8 bit video processing board (AP), 302 capable of digitizing the pixel values of the RS-170 video signal in real time, and generating video from data stored previously, and three frame buffer boards, arranged as one 8 bit (FB 0) 308, and one 16 bit deep image buffer (FB 2) 310 for temporary storage of image data.

One Arithmetic Logic Unit (ALU) board 304, is used to perform logic and arithmetic operations on images stored in the frame buffers. Every image passing through the ALU takes 1/30th of a second, so simple image calculations can be performed faster by using the ALU instead of the computer hardware.

The boards are housed in an extension to the computer bus used to control acquisition and processing. They are controlled with the use of library functions called from Fortran language programs.

In the acquisition mode the RS-170 video signal is generated in the camera 36, then fed to the AP board 40 and the video sync/motor circuitry 18 (FIG. 1). As the board digitizes images at a rate of 30 per second the pixel gray values go through a look up table adjustment to linearize the response of the system. The video output of the AP board 302 (FIG. 9) is observed on a monitor 38 by the user and is available at the input of the optical disk recorder 44 for storage. Programs written in Fortran an in assembler language control the sequence of events in the process of acquiring all needed data for subsequent processing.

After the images have been stored in the optical disk 44, and the strobe intensity data as a file in the computer, the calcium images can be processed in the same system. For processing, the video output of the optical disk 44 is connected to the AP board 302, and the ALU and 304 frame buffer boards 308, 310 are used. The real time acquisition control will be explained in detail.

When digitizing images from the optical disk recorder 44 the source of video should be set as a "master" (internal sync generation), and the AP board 302 as a "slave" (extract sync pulses from external video signal). In this way, appropriate timing relations are conserved and jitter free images can be acquired.

Figure 10:
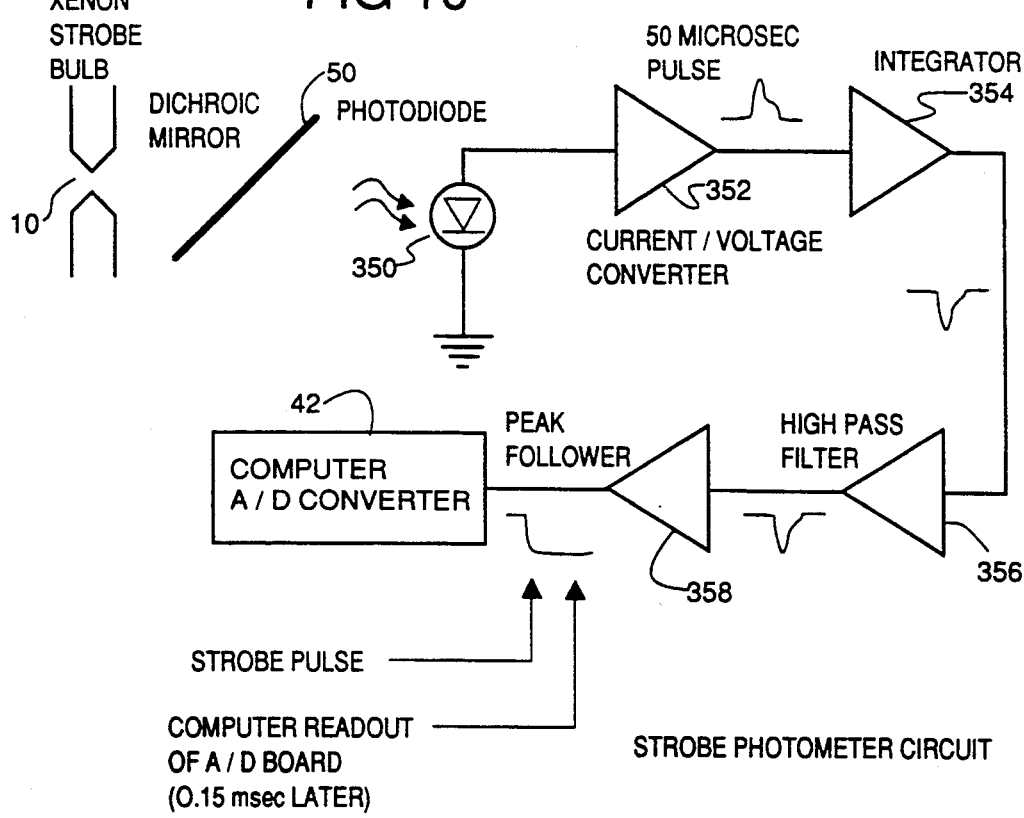
FIG. 10 is a block diagram of an embodiment of the photometer shown in FIG. 1.
Figure 17:
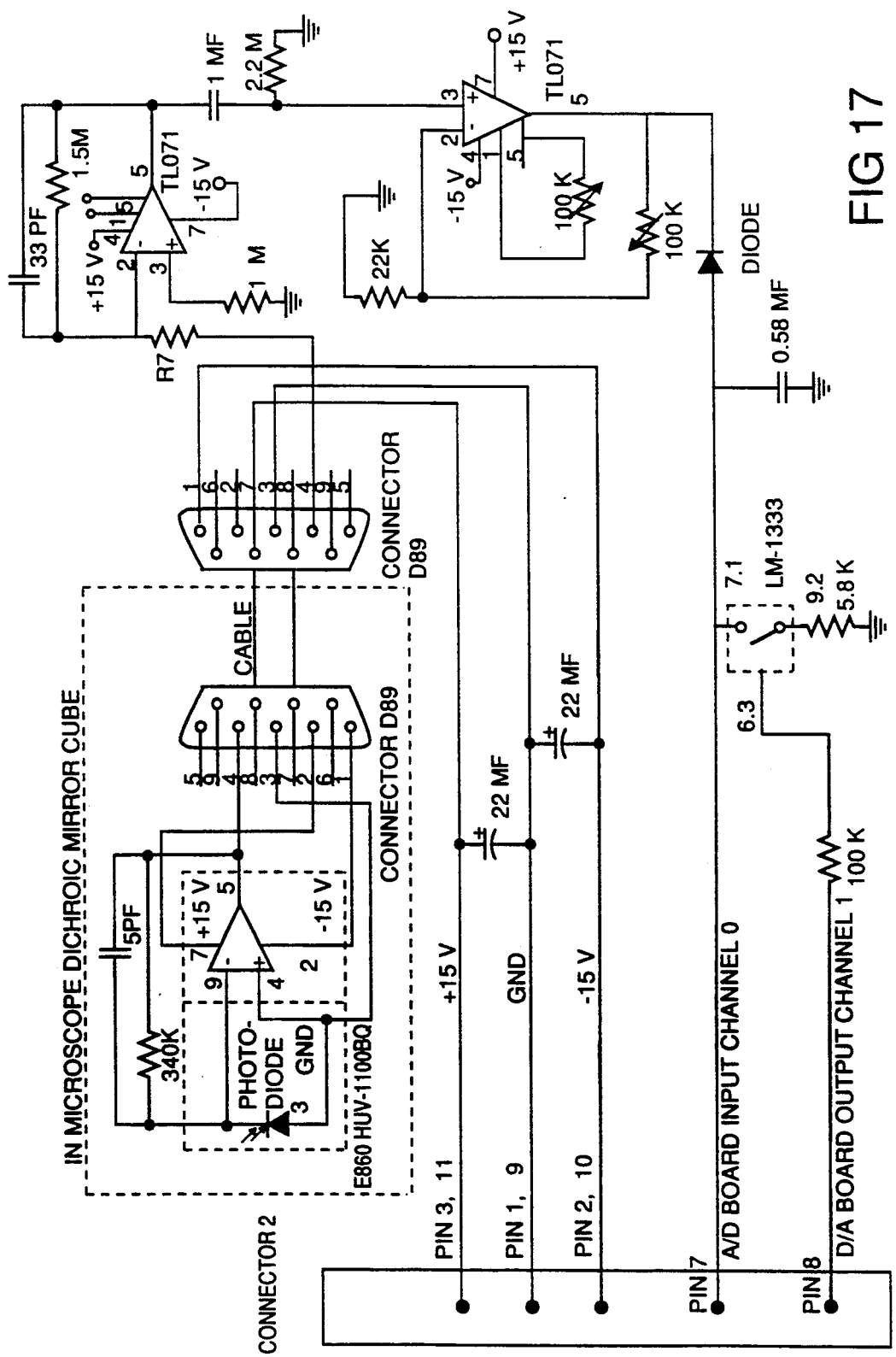
FIG. 17 is a schematic diagram for an embodiment of the photometer for the embodiment of the system shown in FIG. 1.

Preliminary calibration data indicated that there were significant variations in strobe power, even during steady periodic flashing. A circuit to monitor the power of each flash, and record the actual values of the strobe exposure in a file to normalize the images in the processing stage is shown in FIGS. 10 and 17. A U.V. sensitive photodiode 350 was placed in the illumination optical path behind the dichroic mirror 50, so that it would read strobe output after the interference filters. Since the amount of fluorescent intensity from the sample is directly proportional to the excitation input power, it is very important to monitor any variations.

The U.V. sensitive photodiode 350 (model HUV1100BQ, by EG&G) includes an op amp 352 used as a current to voltage converter in the same package. The output of the diode 350 located in the microscope is relayed through a shielded cable to the rest of the circuitry, located on a wire-wrapped board in the computer case. The output pulse from the photodiode 352 is proportional to the intensity of the flash, and is about 50 microseconds in duration. This signal is integrated by integrator 354 to find the total light exposure, and then passed through a high pass frequency filter 356 (pass frequency above 0.07 Hz) to discard any dark current from the photodiode 350, or integrator bias drifting. The signal gain and offset are controlled by a non-inverting amplifier before feeding it to a peak follower 356 with a long time constant (4.6 msec) to hold the analog value until the computer is ready to read it using an A/D port 42 (about 150 microseconds).

Since the amounts of data generated in real time require a large amount of storage, a high resolution optical disk recorder (ODR) is used for real time storage of the data. For example, 1 second worth of data at 8 bits/pixel in (512 * 512 pixels) requires a throughput of:

(512*512) bytes/image*30 images/second = 7.9 megabytes/second

At this rate a typical experiment that lasts anywhere from 3 to 8 minutes would need between 1.4 and 3.8 gigabytes of digital storage. Therefore an analog optical disk recorder 44 is used. In one embodiment, the recorder is a Panasonic model TQ-2025F with a capacity to store up to 8.8 minutes of data at video rates (16,000 frames). During acquisition, the ODR is set to the automatic record mode (will record under control of a computer TTL signal). For the processing it is necessary to step through and display each image continuously while the AP board digitizes it. It has a resolution of 460 T.V. lines, and is stable enough to provide accurate reproduction of the images stored, even in a freeze-frame mode (continuous display of single frame). Our tests showed that the noise introduced by the disk storage/retrieval process was under 0.6% per pixel if 100 images were averaged by the AP board 302 while the disk player is in freeze-frame mode. To maintain processing speed and avoid buffer overflow we average 16 equal frames from the ODR at processing time. Protocol software was written interface with the ODR through a serial RS-232 port. A modification to the ODR circuitry was made to allow the switching of the synchronization source under computer control, via a TTL signal.

In this embodiment Digital Equipment Corporation PDP 11/73 computer 42 is used for real time control of the acquisition process, and later as the environment for off-line processing of the data. It is equipped with a magnetic tape unit for permanent massive storage, 4 megabytes of memory, a Data Translation A/D and D/A board (model DT2605), and the set of imaging boards from Imaging Technology.

The software which controls the process of data storage during the biological experiments is a combination of Fortran and PDP assembler code. The assembler language routines command the interface board, while Fortran programs display menus, make real time calculations, handle file storage, and make calls to the lower level routines. Within the environment of IMTECH, a program written to automate image acquisition at the microscope stations, new routines were added to the menu and several other modified to adapt them to the fast imaging mode. Among these are routines to control the optical disk, the computer interface board, and the imaging boards.

The Acquisition software can be divided into three sections, Initialization, Storage, and Completion.

Referring to FIG. 11 during Initialization the following steps are taken:

1) Communication is established between the computer and the ODR (Step 400).

2) A correction look up table is loaded in the digitizing board to linearize camera input (Step 402).

3) An empty space appropriate for the size of the experiment is located in the ODR (Step 404).

4) The user is guided to a menu where he may set all the parameters of the experiment, such as number of frames, gain of photometer recorder, calibration information, and name of file to store experiment information (Step 406).

5) The user is allowed to check the fluorescent images before recording images in two different modes, as single frames as the strobe gives a ten flash burst, or as averaged images obtained by adding several odd fields together for up to 128 times (Step 408). This second option dramatically reduces noise in the image at the expense of time resolution. Also at this point strobe intensity and image intensifier persistence statistics are calculated. The persistence is calculated by flashing the strobe as the even field information is leaving the camera. Without any phosphor persistence, only the odd fields should be affected by the flash. In the resulting image the odd lines have the true intensity value due to the flash, and the value of the even lines is related to the persistence left behind. The ratio of the value of the even field over the previous odd field gives the "lag" factor. This can be kept to a minimum by adjusting the gain of the image intensifier.

All software timing during the storage cycle is referenced to the video signal blanking pulses (vertical blank VB, and horizontal blank HB). The AP board generates the blanking pulses, and both the camera and the ODR synchronize to them. To avoid timing errors all computer interrupts are disabled during this period.

During the storage phase the storage algorithm is executed a predetermined number (I times) of time (FIG. 12).

1) Wait for beginning of even field, then wait for 20 horizontal blanking periods (HBs) to allow for transfer of previous field from active zone in CCD chip (Step 450).

2) Read filter position (Step 452).

3) Fire strobe flash, then wait 2 HBs for photometer integration to take place (Step 454).

4) Read value from strobe photometer (Step 456).

5) Wait for beginning of odd field, and 20 HBs more (Step 458).

6) Fire strobe flash, and wait 2 HBs (Step 460).

7) Read photometer value, and save in array (Step 462).

8) Read filter position, if same as last no filter position error occurred (Step 464).

9) Put marker on image to identify wavelength of excitation filter (Step 461).

10) If n greater than 2 but less than (ITIMES-1) record image in ODR. The first two images without flash can be used to calculate dark current noise, and the last one has experiment data for late reference (Step 468).

The Completion algorithm (FIG. 13) follows the sequence:

1) Store data from photometer on file (Step 480).

2) Create image with user's data and photometer statistics to be saved as last image of experiment (Step 482).

3) Return control to user and display menu (Step 484).

Tests were performed on the individual components of the dual excitation wavelength microscope to assess the linearity and noise contributions of each section. It was tested as a whole with calibration solutions to estimate dynamic range, linearity, stability and spatial resolution.

The camera was tested to check manufacturers specifications, regarding linearity, timing, and sensitivity. The linearity is expressed by the "gamma factor" of the camera. Gamma (g) is the exponent of the power function that relates output response (Y) to light input (X) on the sensor, that is:

$$Y = K * (X)^g, K = constant$$

Even though charge coupled devices are inherently linear in their response to light, in most RS-170 standard cameras circuitry is added to allow for adjustment of gamma.

To measure linearity, a set of neutral density (ND) filters was used to control the light reaching the camera. The ND filters are classified by their optical density (OD), that is, the negative logarithm of the transmittance (T). As the transmittance was decreased, the digitized count (0>255) given by the AP board was recorded at least twice per filter.

$$T = (light\ intensity\ out) / (light\ intensity\ in)$$

$$OD = -Log\ (T)$$

A set of relative intensity (% intensity) values was obtained by switching ND filters ranging from OD=0.04 (94%) to OD=2.0 (1%) in the excitation path.

The camera response was extremely non-linear within the range of digitization of the board. With information provided by the manufacturer the camera's input/output response was linearized by calibrating potentiometers in the internal circuitry. The AP board was also calibrated to match the dynamic range of the camera video output signal.

The intensity measured when there is no light input corresponds to the "dark current" level of the sensor.

The AP board as previously described, can transform the digitized values for the video while the images are been acquired continuously. The AP board digitizes the video signal to 8 bits of precision assigning grey levels ranging from 0 to 255 for every pixel. This digitized value is then used as a pointer to a table where substitute values can be stored. When no transformation is required, the Look Up Table (LUT) locations are filled with the same value as the pointer, so the effective numerical output is equal to the grey level input.

The video output of the AP board is delayed by one complete frame with respect to the camera. If a transformation function is loaded into the LUT, the modified video will emerge from the AP board one frame later. An appropriate function was used to linearize the response of the system to changes in light input.

From the data a model was fit with a third degree polynomial.

$$Y = 9.02 + 2.29X + 0.0265X^2 + 0.00026X^3$$

where X is percent intensity, and Y is the original A/D count obtained without any LUT change. The inverse function was found to be:

$$X = -5.1719 + 0.5444Y - 0.0027Y^2 + 0.0000089Y^3$$

To obtain a linear response, this curve is transformed into a function of the form:

$$Y^* = mX + b,$$

where
m = slope −(255−9)/100 = 2.46
b = intercept = 9 and $$X = (Y^* - 9) / 2.46,$$

where $Y^*$ is the transformed (linearized) value.

Combining these two equations yields:

$$Y^* = -3.723 + 1.338Y - 0.006642Y^2 + 0.00002186Y^3$$

To provide a zero start for both variables the independent term (−3.723) was dropped in the system implementation. With this transformation, optimum use of the dynamic range and linearity is obtained. The final response values were obtained at different image intensifier gain settings.

The output phosphor of the image intensifier can be over-excited and retain phosphorescence for more than 16 milliseconds after excitation. This is enough time to corrupt the next video image with data from the previous flash. It is important to monitor this lag phenomena to avoid a response not related to light input. We obtained a measure of it by monitoring the percent contribution of one video field into the next. It was found that the lag function itself fits well a double exponential decay. In a field transfer camera, the integration cycles for the even and odd fields do not overlap. It is possible to measure the lag by running a test several times in which the strobe is fired to provide information exclusively in the odd field, and then measuring both the odd and even after it. It is observed that in the linear region the odd field values follow linearly any increase in light input and there is no contribution of the phosphor persistence into the even field.

As the intensity is increased the digitized value for the odd field is clipped to a saturation value (close to 255), and the even field digitized value also increases. It should be noted that the linearity of the intensifier is only tested together with the camera at the input stage, and that the linearity of the intensifier is inferred from the camera-intensifier assembly after correcting for the camera response according to the previous section.

During operation the user has the chance to check the lag values in the real image just before recording. The user can check the image with strobe bursts, to get an image of the cell in the monitor. Then, a window of variable size can be moved across the screen to the brightest spot in the image, and the lag test performed only with data from within this window. The user can then adjust the II setting or the strobe intensity to minimize the lag.

Figure 14:
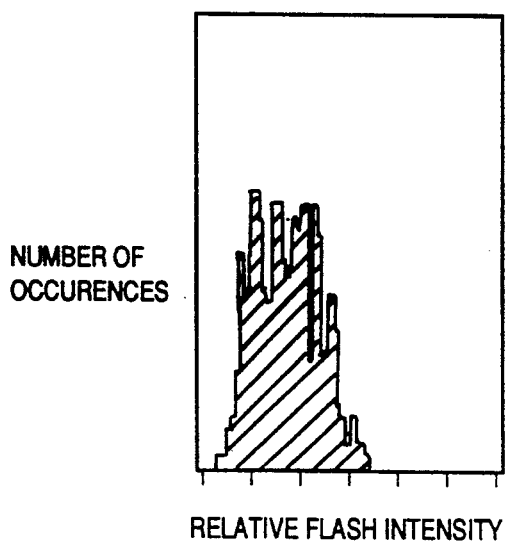
FIG. 14 is a histogram output of the UV source of the embodiment shown in FIG. 1.

The power output of the strobe/filter complex varies between individual flashes. The distribution probability function was found by running tests using the strobe photometer described previously and storing the values obtained during the experiment. Our studies on two different commercial models of Xenon strobes showed that the probability distribution of the events was almost uniform in shape with a standard deviation running anywhere from 10% to 25%, depending on factors such as the device manufacturer, age of bulb and power per flash. FIG. 14 shows the probability distribution function for 400 consecutive flashes.

From the data the linearity of the image acquisition setup was studied. A variable d.c. bulb light source with a green filter (to approximate the 510 emission of the probe) was located over the objective in the microscope, and with neutral density filters a response versus light input curve was constructed. For any given intensifier setting the response curve is linear. Since the intensifier setting does not change within individual experiments this response is quite appropriate for our purposes. The A/D counts read by the video digitizer represent the fluorescent intensity of the probe. The background values were around 7.5 counts for all II settings.

The relationship between the intensity of the Xenon arc flash and intensity measured by our custom-made photometer (as read by the 12 bit A/D converter) was determined. The strobe was flashed 32 times while the excitation intensity was limited with ND filters. The average of the strobe photometer for the 32 flashes was recorded and plotted against relative light intensity.

The linearity of this relationship is important since the strobe intensity values detected with this photometer will be used in the image processing. The photometer data is necessary to correct for errors induced by the variations in excitation intensity between the different frames of the same experiment.

Another important measure is the gain stability, that is, the consistency of a light intensity measurement given a stable input. The purpose of this test is to check for possible changes in gain or sensitivity over several minutes (low frequency). In this case a known concentration of fluorescent solution was located on a calibration chamber over the objective, the strobe was fired 16 times, and average fluorescence output of a 100*100 pixel box of the digitized image was measured, together with the strobe intensity for those flashes. The response was taken at 3 different levels of light intensity to cover the dynamic range of the system. The standard deviation for the eight measurements was 3.2, 2.2, and 1.6 counts respectively. When the data were normalized by taking into account the strobe intensity the results were even more consistent, with a standard deviation of only 1.6 counts (out of 255).

As a measure of motor control reliability the motor was turned on and left running for a 5 minute period. The motor was left to run in synchrony with the video signal for 30 minutes while the output of the motor position sensor was observed on a long persistence storage oscilloscope. The video signal reference was used to trigger the oscilloscope trace as a fixed timing reference. The variation in phase of the motor could be measured as the section overwritten by the storage trace with respect to the total revolution period (66 milliseconds). It was found that the typical variation (standard deviation) was equal to 2.0 milliseconds, and the absolute maximum variation within a 30 minute period was 4.5 ms. This would correspond to a standard deviation of 10.8 degrees and an absolute maximum of 24.3 degrees.

The timing of the strobe flash with respect to the motor rotation has a maximum tolerance of $+-33.5$ degrees, before the strobe will flash on the wrong filter. Hence, this level of precision satisfies the system specifications.

A measure of image quality for quantitative microscopy is the signal to noise ratio (SNR). The predominant sources of noise in the low light imaging system described are:

Signal dependent noise (shot noise) which has a Poisson distribution. Because of the low detector quantum efficiency and limited photon counts, signal to noise is ultimately limited by this uncertainty. The photoelectron signal standard deviation in a given pixel or region of pixels is equal to the square root of the number of photoelectrons detected (n). The first detector surface (the S-20 photocathode of the image intensifier), will have a signal to noise of $(n)^{\frac{1}{2}}$ at best. The intensification steps will amplify the signal enough to be detected by the CCD area sensor, and will diminish the SNR slightly since the gain at each stage is very high. Moreover, other signal independent noise components will corrupt the image further.

The dark current of the intensifier has Poisson distribution and a very low event count. For the tube used it increases exponentially with temperature, by an order of magnitude for every 10 degrees. Photoelectrons released thermally at the photocathode are also accelerated and amplified through the intensifier stages.

The dark current of camera sensor, which has a Gaussian distribution with a positive mean. It is due to thermal generation of electrons in the CCD sensor and cannot be discriminated from the electrons formed from incoming photons.

Signal to Noise can be measured from acquired data in two equal images. If two flat fields of equal illumination are imaged and digitized, the statistics of the noise corruption process can be extracted from the difference of two flat field images.

First, the flat field image is modelled as a deterministic signal plus an additive noise value. Every pixel in the image is a random variable undergoing the same process. The overall mean of this ensemble is equal to the signal, and the standard deviation is a measure of the noise. Since the measurement is taken over several hundred pixels, the statistics are Gaussian in nature according to the Central Limit Theorem. Given image 1 (IM1), and image 2 (IM2), their pixel by pixel difference image is an ensemble of the additive noise process.

$$SNR = \frac{(\text{mean}(IM1 + IM2)) - \text{Background}}{((2)^{\frac{1}{2}} * \text{stddev}(IM1 - IM2))}$$

The difference image should have zero mean, and a variance equal to twice the variance (noise) of a single image. Therefore, the standard deviation from the difference image has to be scaled by $(2)^{\frac{1}{2}}$. The use of a difference image for statistical calculations is not related to local sensitivity or illumination variations, as long as these are common to both images. Since the difference operation is performed on a pixel by pixel basis, the contributions of each pixel to the total deviation is measured with respect to the local pixel mean.

In our case, fluorescence cell images are seen as bright cells over a fairly wide dark background. Signal to Noise can be best measured in this situation by subtracting two equal images of a cell at rest (no movement in between). The statistics can be calculated from a box located inside the cell in the area of interest. This was done using calcium concentration images, which were calculated from fluorescently labelled cells. The $Ca^{++}$ concentration is almost homogeneous within unstimulated (or fully contracted) cells, so small areas within them can be treated as flat fields for the purpose of SNR calculation. The SNR calculation. The SNR calculated by this approach has the advantage of including uncertainties from both the acquisition and processing stage.

The following values for SNR and Calcium concentration were determined within the same small area in a cell using a 30*30 pixel box (approximately 3*3 microns box). These values are from 5 pairs of images of the same cell, after applying all the processing steps (to be described) to obtain calcium concentrations. Five measurements of SNR were made according to the previous formula using two images for each measurement. The average SNR and its standard deviation is shown for a cell at rest and then totally contracted. The mean $[Ca^{++}]$ corresponds to the average calcium value for the same 10 images.

| Cell at rest: | Mean $[Ca^{++}]$ = (188 + − 7) nM |
| (n = 10) | Image SNR = 10.4 + − 1.8 |
| Cell contracted: | Mean $[Ca^{++}]$ = 479 + − 19 nM |
| (n = 10) | Image SNR = 13.3 + − 1.6 |

These values for calcium concentration are reasonable for smooth muscle cells. The confidence in this calcium concentration value, can be increased by summing the values at the two wavelengths for a few images before taking their ratio. If N images are averaged, the error will decrease by a factor of $(N)^{\frac{1}{2}}$. However, such an average will decrease the time resolution attainable with the microscope. Another way to improve the data confidence is by summing together more pixels (again, before the ratio calculation), with the subsequent loss of spatial resolution. As the cell contracts or moves responding to external stimuli, the error will increase mostly in the boundaries of the cell since some displacement has occurred from one wavelength image to the next.

The imaging system described has several components: optics, image intensifier, and CCD camera sensor. All of these contribute to the blurring of the image with their own Modulation Transfer Function (MTF).

The MTF is the spatial Fourier Transform of the Point Spread Function (PSF). The PSF is the image of a single point source as it goes through the system components. In the system described the ultimate limiting factor is the spatial resolution of the image intensifier complex. The PSF of the image intensifier is much wider than any of the other components, and is oversampled by the camera pixel grating.

The spatial resolution, as defined by Rayleigh, is the smallest distance between two individually resolvable point sources. This implies that their point spread functions can overlap until the "dip" in between them is at least 5% of the peak values. We shall use this criterion for resolution even though it does not take into account image noise. Noise will further limit resolution. The uncertainty related to pixel values (noise) determines what structures are "resolvable" or what changes are statistically relevant.

Figure 4:
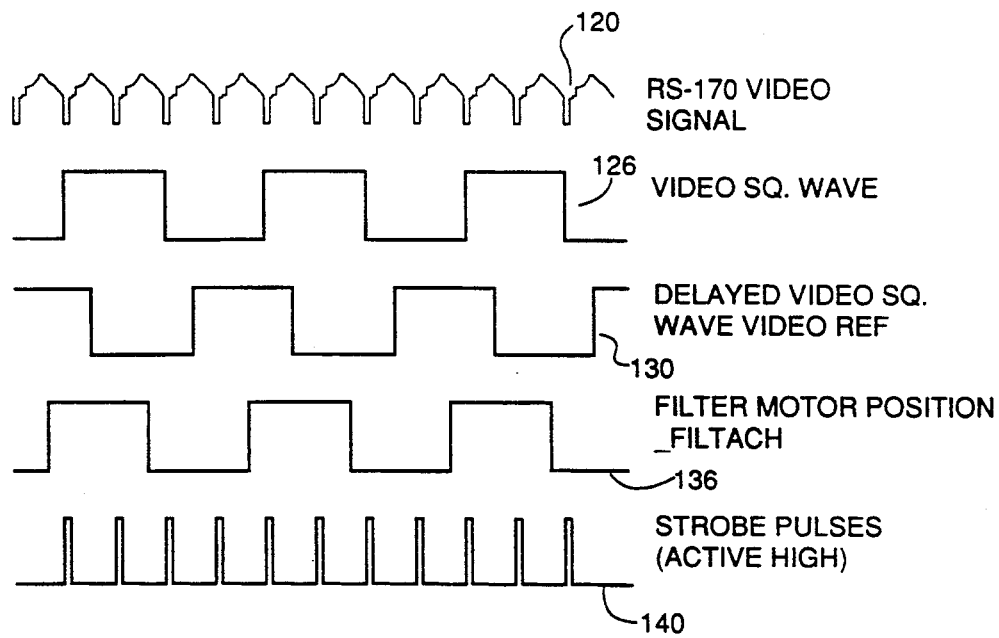
FIG. 4 is a timing diagram for the embodiment of the motor control of FIG. 3.

The point spread function, as shown in FIG. 4.9, includes the effects of the image intensifier, camera, and digitizing boards. The microscope itself is not included, but it should not affect the results since the transverse optical resolution is of the order of 0.2 microns for green 510 nonometer light (Rayleigh criterion).

The ideal microscope resolution is given by 0.61 * lambda / N.A.

So for a numerical aperture (N.A.) of 1.3 and a wavelength of emission of lambda = 510 nm, the ideal microscope resolution is equal to 0.24 microns.

This is an ideal limiting case, but as we will see, it is still much smaller than the resolution of the Image Intensifier.

The PSF was measured by imaging a 1 mm pinhole in front of a green light emitting diode at distance of approximately 6 feet away. It was still small enough to be considered a point source, and the curve obtained is symmetrical and gaussian in appearance.

A Gaussian curve fit to this normalized function has a correlation coefficient of r = 0.999, with the coefficients:

$$Y = 99.6 * exp(-0.1699 X^2),$$

corresponding to a variance of $VAR1 = 2.94$ pixels$^2$

During the image processing, a Gaussian filter is used to reduce the noise in the images before ratiometric calculations, this step improves signal to noise at the cost of spatial resolution. We can estimate the effect of this filter in the spatial resolution response mathematically.

The Gaussian filter convolved with the images at the processing stage has a variance (VAR2) of 2.25 pixels$^2$. The convolution of two gaussian functions results in another gaussian with variance equal to the sum of the previous ones. The spatial frequency response of the system, including image intensifier response (PSF) and smoothing is a Gaussian function with a variance equal to the sum.

Adding the variances from the PSF and the smoothing filter:

$$VAR = VAR1 + VAR2 = 2.94 + 2.25 = 5.19$$

The combined Gaussian function is:

$$Y = K \exp(-X^2 / (2 * 5.2))$$

For Rayleigh criteria, and K=1, Y should be:

$$Y = 0.95 / 2 = 0.475 \ (a \ dip \ of \ 0.95)$$

The resolution is twice the distance in X, the inverse combined Gaussian function is:

$$Res = 2 * X = 2 * (-(Ln(0.475) * 10.4))^{0.5}$$

$$Res = 5.56 \ pixels.$$

With an 40× objective lens and a 12.5× ocular, the pixel to object relationship was found by digitizing an image of a micrometer slide, and counting the number of pixels per micrometer division. It was found to be approximately 1 pixel per 0.2 microns (sample plane). Therefore the resolution can be better expressed as 1.12 microns.

The processing of the images stored in the optical disk recorder is done in the same system used for image acquisition. The goal of the post-processing is to provide a sequence of ion concentration images from the individual wavelength images stored in the optical disk.

The approach taken in writing the software has been to emphasize speed by making reasonable assumptions with respect to the nature of the images, and using integer arithmetic at some steps of the processing. The PDP 11/73 computer used in the system is limited in speed and storage capacity compared to most workstations available today. The data acquired can be analyzed through the use of the described processing steps, and if it is found to be biologically relevant, a series of interest may be transferred to another computer for detailed examination.

The processing software is a stand alone program written in Fortran which carries out file handling, optical disk communications, and image processing. The processing includes floating point operations and integer operations done by pre-programming the ALU to speed up the calculations. The images are retrieved from the ODR by averaging the same "still" frame using the image digitizing board (AP board) 16 times. By averaging, the introduction of extra noise by the ODR is reduced considerably. To boost the processing speed, the size of the original images (512 * 480 pixels) is reduced by half in the X and Y directions. The reduction does not lead to a loss in resolution since the point spread function of the image intensifier is already wider than twice the sampling period of the AP board. The reduction by a factor of two in the X and Y directions allows more than one unprocessed image to remain in a single frame buffer during processing. The 256 * 240 pixel images can be processed faster and the memory storage capacity optimized for long processing sessions.

The images are stored in the optical disk in a sequential manner with alternating 340 nm images. To be able to recognize the excitation wavelength of each image, a marker was inserted at acquisition time at the bottom left corner of the images (white for 340 nm and black for 380 nm). A file containing the values for exposure as detected by the strobe photometer was stored in the computer disk to allow for corrections due to strobe variations.

Figure 15:
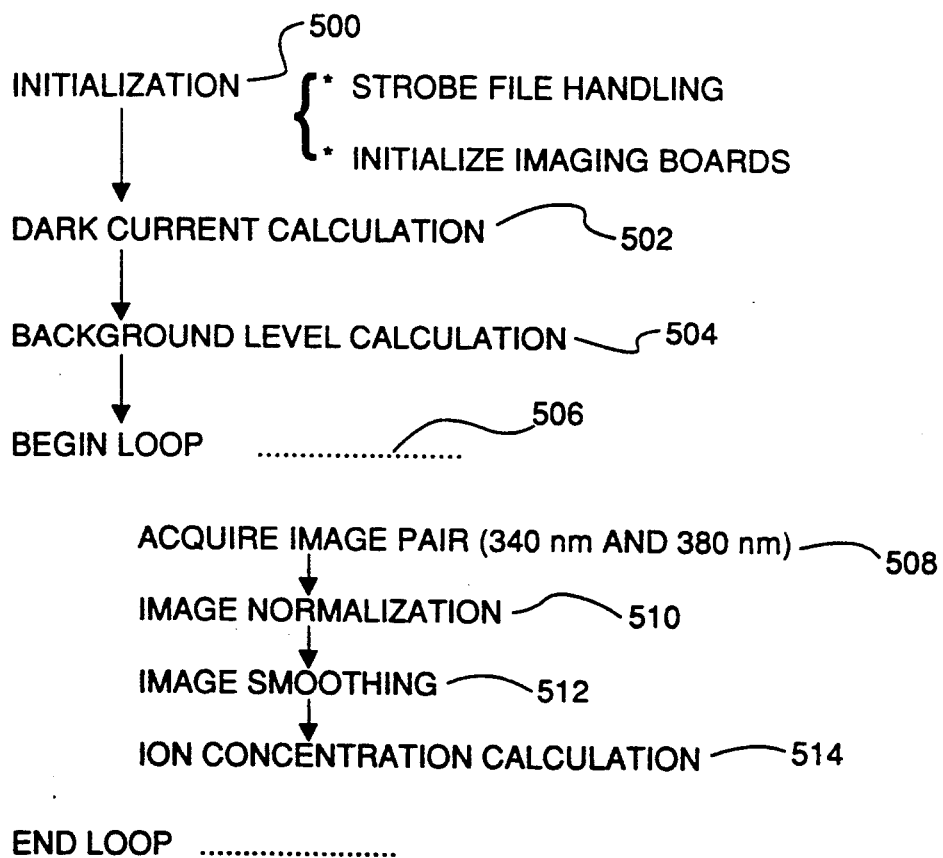
FIG. 15 is a flow diagram for an embodiment of the main program algorithm for the embodiment of the system shown in FIG. 1.

The processing involves four major routines under control of a main program. Other assorted routines are needed to take care of data handling and user interface. These are called by both the main program and the processing major routines. The main program is shown in FIG. 15.

The images of an experiment have been saved in the following manner:

```
Frame #:
1     2       3       4       5     ... N
no strobe 340 nm 380 nm 340 nm ... Exp. data
```

For processing purposes at least four consecutive images have to be retained in memory at any given time. The images are grabbed from the optical disk sequentially in pairs, and then are cycled in a first in/first out fashion until the last one is processed.

In this first stage the main program initializes the system (Step 500). Initialization includes the following steps:

1) All imaging boards are initialized to default memory addresses and the frame buffer and ALU video channels are set to known values before the processing can start.

2) The user is asked for the experiment file name. Then the file is retrieved from computer disk. This file contains calibration constants, optical disk location and size of experiment image data, user comments, and the values for strobe intensity at each frame of the experiment. The calibration constants: Rmin, Rmax and Beta are retrieved from the file header. If they were not stored at acquisition time, they can be introduced at this point. These parameters are used in the last step of processing, where the calcium concentration is calculated.

3) The disk is positioned at the starting frame of the experiment and the user is allowed to "browse" through the optical disk images under computer control. When an appropriate starting frame has been found the user may start processing.

4) Given the starting location and the number of frames to be processed, an array (ISTROBE) containing the values for the strobe exposure of each frame is accessed to find an average exposure value for the 340 nm images (AVG340) and for the 380 nm images (AVG380) within the images to be processed. These constants will be used in the normalization process detailed later. Also the offset value (PHTOFF), is obtained from the first two values stored in the experiment. They correspond to the photometer reading without a strobe flash, which should be low if the circuitry is properly calibrated.

Next the system dark current calculated 502. This is defined as the reading obtained from the camera/intensifier complex without any excitation. At acquisition time, the first two frames of the experiment were stored in the optical disk without any strobe flash, and can be used for calculating the dark current. This signal is independent of the sample and the excitation and are subtracted from the pixel values as the very first step in the processing. The following steps are taken:

1) The optical disk is commanded to show frame #1 of the experiment series, and acquisition starts by summing 16 times the same frame into a 16 bit frame buffer (FB 2). This is done to minimize electronic noise in the playback process from the ODR.

2) The process is repeated with frame #2 and added to the previous one in FB 2.

3) The mean pixel value of the image is calculated. This corresponds to the dark current multiplied by a factor of 32 (corresponding to the number of frames added). This mean value is divided by two (IDARK), and used as the dark current value for 16 frames in subsequent steps of processing. The substraction is done automatically when the images are retrieved from the optical disk by setting the frame buffer value to negative IDARK before starting the summing process into the same FB 2.

Next the Background calculation 504 is made. The images of fluorescent cells in the microscope appear as bright regions over a larger dark field. The fluorescence signal emanating from the cell, is corrupted by background fluorescence at acquisition time.

The intensity of the image in any given area is the sum of fluorescence due to the probe in the target cell plus background signal generated by the optics, and the cell incubation media. This media includes nutrients necessary to keep the cells alive during the study, and may contain dye that has leaked out of the cells, or it may have some fluorescence of its own.

The background statistics (mean and standard deviation) are calculated from the first 340 nm and 380 nm images of the group to be processed. This background fluorescence mean is also subtracted from the image, since it appears as a bias value on top of the signal. The standard deviation of the background is used to isolate cell pixels from background pixels in the calcium calculation.

To speed up calculations, the values for the backgrounds signal (one for 340 nm and one for 380 nm) are calculated in advance using a pair of images, and then applied to all images obtained in the same experiment under identical conditions.

To calculate the background values automatically, the background fluorescence is assumed to follow a gaussian distribution. To find the mean and the standard deviation of the process a series of steps are taken:

1) A 380 nm (or 340 nm) image is digitized, reduced and normalized to a 256*240 pixel size. The normalization step is explained in detail in the next section.

2) The grey level distribution (histogram) of the image is calculated. That is, a plot of frequency of events (pixels) versus grey level intensity over the entire image.

3) Next, the highest peak in the histogram distribution is found. This value corresponds to the grey level with the highest number of pixels. From this peak the routine searches on both sides of it for the points at which the number of pixels has decreased to more than 61% of peak value.

Using only the pixels within these boundaries, the mean is calculated (IBK340 and IBK380), and a more precise value for the 61% level is found by linear interpolation. Assuming the process to be gaussian in nature, the 61% window on both sides should correspond to twice the standard deviation (IDEV) of the process. These values describe the distribution of the majority of pixels in the image and are representative of the background process occurring all over the image. It is a signal independent random variable whose mean acts as a d.c. bias on every pixel and it's standard deviation corresponds to signal independent noise. This noise reveals itself as an uncertainty assigned to the values for fluorescent intensity emanating from the cell and is independent from cell fluorescence.

Once the data acquisition loop 506 begins, an image is acquired at both wavelength 508.

Once a pair of images have been acquired from the ODR they are reduced and normalized 510 according to the flash exposure value for the specific frame. A pixel is generated from 4 original pixels by addition. As they are added the individual values are normalized according to the strobe intensity value corresponding to that image frame (and field). The full size image is scanned every two pixels in both directions, and a compressed image created in the top left corner of FB 2.

An intensity for pixel (x,y) in frame n (340 nm image) undergoes the following transformation:

$$N(x,y,n) = [(AVG340 * X) - IBK340],$$

Where $$X = \frac{[O(x,y,n) + O(x+1,y,n)]}{ISTROBE(n,1)} + \frac{[O(x,y+1,n) + O(x+1,y+1,n)]}{ISTROBE(n,2)}$$

N(x,y,n) = normalized value for pixel (x,y) of frame n
O(x,y,n) = original image at pixel (x,y) of frame n (already dark current subtracted
IBK340 = image background mean found previously
AVG340 = mean of the strobe exposure values for 340 nm excitation
ISTROBE(n,1) = value of strobe exposure corresponding to frame n, odd field
ISTROBE(n,2) = same for the even field.

This is done at all pixels and has the effect of compressing and normalizing the data to a standard mean intensity. Then the grey level values from different images can be directly compared with each of the, and truly represent the fluorescent intensity due to the probe. The same calculation is carried out for the 380 nm image using the 380 nm strobe photometer average and mean image background (AVG380, IBK340) instead. This routine is called twice per loop pass; once for each wavelength. The normalized images resulting from this step are saved in computer virtual memory to be used in the next round of processing.

To improve the signal to noise ratio the images are subject to low pass filtering (smoothing) 512 in both the spatial (x,y) and in the time domain. This process is done on the individual wavelength images before the ratio calculation.

In the time domain a moving average filter can be implemented by the sum of the present image plus the last image of the wavelength. However this option will cut time resolution by a factor of $(2)^{\frac{1}{2}}$, so it can be disabled for processing rapidly moving cells. After the normalization step the images (N(n) and N(N+1) are placed in the top of the 16 bit frame buffer (FB2). The previous two normalized images, N9(n-2) and N(n-1) are retrieved from virtual memory and added to these pixel by pixel.

$$S'(x,y,n) = N(x,y,n) + N(x,y,n-2)$$

and, $$S'(x,y,n+1) = N(x,y,n+1) + N(x,y,n-1),$$

where

S'(x,y,n) = Time-smoothed 340 image pixel
S'(x,y,n+1) = Time-smoothed 380 image pixel
N(x,y,n), N(x,y,n−2) = pixels of normalized 340 image
N(x,y,n+1), N(x,y,n−1) = same for 380 image In the spatial domain, a low pass (gaussian) filter with a standard deviation of 1.5 pixels is convolved with the image. The program takes advantage of the hardware architecture by defining the convolution kernel (5*5 pixels), and using the ALU board to perform the operation. Both wavelength images fit in FB 2 at convolution time, and the convolution is performed simultaneously on both. The hardware convolution process is not circular, so the grey values of the border 3 pixels of each image are corrupted by artifacts. This fact, together with the integer nature of the calculations are drawbacks of this approach.

The kernel used in the convolution is given by:

$$KNL(ix,iy) = Integer \{exp [(ix^2+iy^2) / 4.5]\}$$

where, $-2 \leq ix, iy \geq 2$

The convolution over all x,y pixels:

$$S(x,y,n) = \Sigma S'(x-x', y-y') * KNL(ix-x', iy-y')$$

where, $S(x,y,n)$ = filtered image.

After these two steps, normalization and smoothing, the individual wavelength images are ready to be used in the calculation of ion concentration.

The calcium concentration can be found from the relative fluorescent intensities at two wavelengths (340 nm and 380 nm). As explained in previously, the calcium distribution follows the relationship:

$$[Ca^{++}] = Kd * \beta * [(R-Rmin) / (Rmax-R)]$$

With $R - S(x,y,n) / S(x,y,N+1)$

The calculation is performed on a subset of pixels (x,y) of the image, given frame (n) as a 340 nm smoothed image, an (n+1) as a 380 nm image. The subset of pixels for the [Ca++] calculation are chosen to be at least two standard deviation (IDEV) from the 380 nm background fluorescence value. This restriction serves two purposes: it works well as a way of delineating the cell area against background, and provides a certainty of 95% (2 standard deviations in a Gaussian curve) that the pixel used for the calculation corresponds to the cell and not to the background solution.

The approximate values for the constants:

$$Rmin = Ff340 / F^{f340} \approx 0.4$$

$$Rmax = F^{b340} / F^{f380} \approx 5.4$$

$$\beta = F^{f380} / F^{b380} \approx 5.4$$

These depend upon the optical efficiency of the excitation optical path (including objective) for the two different wavelengths. Kd is the calcium dissociation constant and is approximately equal to 220 nM. The calcium concentration values are expected to be within 80 nM and 2 mM for any given cell. So, [Ca++] < is less than 0.002 molar The maximum positive integer contained in the 16 bit frame buffer is 32767. When calculating the calcium image a scaling factor of 10 is used. This calculation assures there are no overflows, and maintains a relationship of one grey level unit per 0.1 nanomolar concentration.

After the calcium concentration files are generated, the images are stored a digital files on magnetic tape and also stored in video format in the optical disk recorder (ODR). The images stored sequentially in the ODR can be viewed as a movie of calcium concentration changes within the cell.

The microscope system was used to image the changes in calcium concentration ([Ca++]) in contracting single smooth muscle cells (from toad stomach) and in white blood cells (from newts). The images of fluorescence at 340 nm and 380 nm were stored sequentially in the ODR and later processed to obtain images of [Ca++].

For each cell, the series of calcium images were assembled into an eight second movie in a single processing run. These time series show distinct regions where changes in calcium concentration take place in the 8 second period. The upper limit on the number of frames that can be processed is only imposed by the amount of storage space available in the hard disk drive of the computer. Longer time series can be made by downloading processed data into magnetic tape as it is generated. [Ca++] images were processed by averaging 4 frames of each wavelength before taking their ratio. The smooth muscle cells were induced to contract by electrical stimulation (60 volts, 10 pulses per second) using a microelectrode positioned adjacent to the cell. The cells were under pulsed electrical stimulation until they started to contract.

The magnification used in gathering the images was 125×, and a full view of a relaxed smooth muscle cell (about 200 micrometers long) is obtained in the field. The results are quite striking; large calcium gradients can be observed in the cell as it is contracting.

The [Ca++] values are consistent with data obtained using spectrofluorometers which provide a single calcium concentration value on whole single cells. The [Ca++] within the cytoplasm rises from 120 nM to 460 nM, while the average [Ca++] value of the whole cell rises to 800 nM when fully contracted.

Motion artifacts appear in the [Ca++] image when the two wavelength images (340 nm and 380 nm) used to calculate the calcium concentration correspond to different time records. If the cell has moved between the time that the two images are collected, they cannot be divided pixel by pixel. Motion artifacts in dual wavelength calcium imaging appear as a bright band on one side of the cell, with a complementary dark band on the other. Motion artifacts are not probable in these cells since the sampling rate of 15 name-pairs per second is much faster than the rate of contraction for these two cells.

We must stress the importance of fast interwavelength sampling, even if single wavelength images are averaged in the processing stage. The averaging process will smooth out large changes in calcium but will not generate motion artifacts. In previous studies of changes in [Ca++] the 340 nm image and the 380 nm image have been recorded in sequence. Silicon intensified cameras (SIT), used commonly in low light level microscopy, are not as sensitive as the intensified CCD used in this work and have a significant persistence. To acquire each individual image using a continuous excitation source, perhaps 0.40 seconds are required. If further time is required to mechanically exchange excitation filters (0.2–0.3 seconds), then the whole image-pair could not be acquired in less than about 1 second.

Other embodiments can include more intense Xenon bulb strobes, or the use of high pressure Xenon bulbs which emit more power specifically in the U.V. range. The power of the excitation bulb could be harnessed with the use of a light guide that covers most of the surface of the bulb as a jacket inside the bulb housing and relays light to the microscope collector to be conveyed to the sample. This also has the advantage of scrambling the light signal, and would provide a more uniform sample illumination.

Another embodiment would balance mechanically the motor shaft and filter and use a more precise proportional-integral control to match the motor transfer function, and minimize the error. Additionally, with a very tightly controlled filter wheel, the wheel itself could be used as a shutter and a continuous arc bulb could be used as a light source. This allows types of studies using the same system without changing hardware, but would require a detector with less persistence than the one presently used.

Detectors with a higher quantum efficiency, and narrower point spread function can also be used. A narrower point spread function would improve the spatial resolution of the system closer to the light diffraction limit of the light microscope (0.24 micrometers). A higher efficiency would provide a better signal to noise ratio, which would improve the reliability on any given pixel measurement.

A further embodiment uses a more powerful computer to perform more complex image processing algorithms. These algorithms should use all the information available to improve the signal to noise of the individual wavelength images before the calcium concentration is calculated. The power spectrum of the fixed noise is calculated from the dark current images and used to minimize the signal independent noise. Signal dependent noise with a Poisson distribution could be reduced somewhat by adaptive filtering. For this purpose the Poisson process constants could be determined from the series of images at the beginning of the experiment, where no movement is expected.

Other information that can be used is related to the dye characteristics, such as the relationship between the changes in intensity at the two measured wavelengths. A local decrease in one wavelength intensity much be accompanied by a proportional increase in the other; this property could provide bounds on the variability of the fluorescent signal allowed within small regions of the cell. The goal of all these approaches is to filter out noise selectively with a minimum effect on spatial resolution.

One embodiment used to improve the time resolution involves the use of large cooled CCD arrays that can store the image data within a masked portion of the chip and be read out later. The linearity and low readout noise of the cooled CCD arrays make them the detector of choice. Pieces of the array can be clocked out of the exposed region of the CCD and into a storage site in about one millisecond. Eight images (390 * 55 pixels) can be obtained in a 390 by 448 pixel CCD chip in this fashion before they have to be read out (which can take 5 seconds).

With enough computing power a system can analyze the images obtained with an intensified video microscope as they are obtained, and can trigger the CCD camera system. The information obtained from the intensified camera can be used to determine when to start/stop the cooled CCD image acquisition. This approach could provide high time resolution of specific local responses while still keeping a longer time record of the environment in which it occurred.

Having shown the preferred embodiments many variations are possible which will still be within the scope and spirit of the claimed invention. Therefore, it is the intention to limit the invention as indicated by the scope of the claims.

What is claimed is:

1. An apparatus for measuring the concentration of an ion in a sample comprising:
   a fluorescent imaging microscope;
   a uv radiation source capable of producing a plurality of uv excitation wavelengths;
   a filter device to select a first and a second excitation wavelength from said plurality of uv excitation wavelengths, said first excitation wavelength capable of exciting fluorescence by said ion in one valence state and said second excitation wavelength capable of exciting fluorescence by said ion in a second valence state;
   a sample chamber to hold a sample for illumination by said radiation of said first and second wavelengths;
   a photometer to measure the intensity of the excitation wavelength being selected by said filter device and to generate an intensity signal representative of the measured intensity;
   a beam splitter to direct a portion of the intensity of said selected wavelength onto said sample to be measured and to direct a second portion of the intensity of said selected wavelength onto said photometer;
   optical elements to collect the fluorescent light emitted by said sample;
   an image intensifier positioned to receive the fluorescent light collected by said optical elements and to produce a intensified image of said sample;
   a video camera to view the intensified image and to produce an electronic signal representative of a frame of said image;
   a frame digitizer to digitize said frame of said electronic signal;
   a synchronizer in communication with said filter device and said video camera to synchronize the selection of one of said excitation wavelengths with the beginning of the production of said frame of said electronic signal by said video camera; and
   a processor in communication with said uv radiation source and said photometer to control the intensity of said uv radiation source and to record the intensity signal produced by said photometer, said computer also in communication with said frame digitizer to process the frame digitized by said frame digitizer and store the processed results on a disk.

2. The apparatus of claim 1 wherein said uv radiation source has a fast rise-time.

3. The apparatus of claim 2 wherein said uv radiation source is a uv strobe.

4. The apparatus of claim 2 wherein said uv radiation source is a uv laser.

5. The apparatus of claim 1 wherein said filter device is a rotatable filter wheel.

6. The apparatus of claim 1 wherein said beam splitter is a dichroic mirror.

7. The apparatus of claim 1 wherein said synchronizer further comprises a filter position sensor to determine which excitation wavelength is being selected and said synchronizer is in communication with said processor.

8. The apparatus of claim 6 wherein said synchronizer comprises a differential amplifier having a first input terminal and a second input terminal, said first input terminal to receive a video synch pulse from said video camera and said second input terminal to receive a position signal from said filter position sensor, said differential amplifier producing an error signal in response thereto.

9. An imaging apparatus comprising:

a fluorescent imaging microscope;

a pulsed uv radiation source capable of producing a plurality of uv excitation wavelengths;

a filter device to select a first and a second excitation wavelength from said plurality of uv excitation wavelengths;

a sample chamber to hold a sample for illumination by said radiation of said first and second wavelengths;

a processor in communication with said radiation source to control the switching on and off of said radiation source in synchrony with the selection of said first and second excitation wavelengths by said filter device.

* * * * *